United States Patent
Fukuhara et al.

(10) Patent No.: US 9,316,942 B2
(45) Date of Patent: Apr. 19, 2016

(54) REFLECTION DETECTION APPARATUS AND APPARATUS USING THE SAME

(71) Applicant: CANON KABUSHIKI KAISHA, Tokyo (JP)

(72) Inventors: Takashi Fukuhara, Higashikurume (JP); Takuya Mukaibara, Susono-shi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/702,474

(22) Filed: May 1, 2015

(65) Prior Publication Data

US 2015/0323882 A1 Nov. 12, 2015

(30) Foreign Application Priority Data

May 7, 2014 (JP) .................................. 2014-096319

(51) Int. Cl.
G03G 15/08 (2006.01)
G01N 21/55 (2014.01)

(52) U.S. Cl.
CPC ............ *G03G 15/0827* (2013.01); *G01N 21/55* (2013.01)

(58) Field of Classification Search
None
See application file for complete search history.

(56) References Cited

U.S. PATENT DOCUMENTS

| 4,989,985 | A | 2/1991 | Hubble, III et al. |
| 6,137,583 | A | 10/2000 | Kim et al. |
| 2010/0266302 | A1* | 10/2010 | Suzuki et al. ................... 399/49 |
| 2013/0094875 | A1* | 4/2013 | Ogata et al. ..................... 399/74 |
| 2014/0308049 | A1 | 10/2014 | Yamaguchi et al. |

FOREIGN PATENT DOCUMENTS

| JP | 02-256076 A | 10/1990 |
| JP | 2000-028527 A | 1/2000 |
| JP | 2002-221495 A | 8/2002 |
| JP | 2013-033181 A | 2/2013 |

* cited by examiner

*Primary Examiner* — Clayton E Laballe
*Assistant Examiner* — Jas Sanghera
(74) *Attorney, Agent, or Firm* — Fitzpatrick, Cella, Harper & Scinto

(57) ABSTRACT

The reflection detection apparatus includes multiple light-receiving elements configured to detect a pattern formed on an object by receiving a reflected light from the object, and a selector configured to select a first light-receiving element group from the multiple light-receiving elements. The selector is configured to select the first light-receiving element group that includes one or more light-receiving elements each mainly receiving a specularly reflected light from an area of the object where no pattern is formed among the multiple light-receiving elements, on a basis of outputs from the multiple light-receiving elements. The detection of the pattern is made on a basis of an output from the first light-receiving element group.

16 Claims, 28 Drawing Sheets

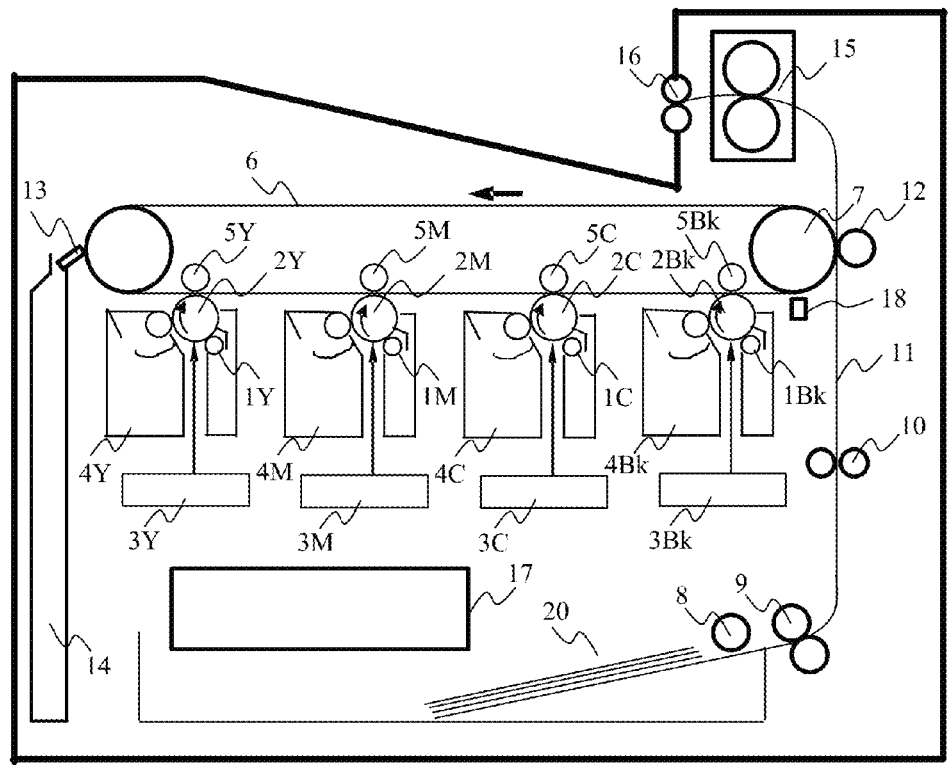
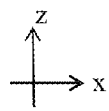
FIG. 1

NORMAL STATE

FIXING POSITION SHIFT

FIXING ANGLE CHANGE

SHIFT IN MOUNT POSITION
OF LIGHT SOURCE

FIG. 7

| REGION SETTING INFORMATION (4bit) | OUTPUT TERMINAL CONNECTED WITH LIGHT-RECEIVING ELEMENTS | | | | | | | | | | | | | | | |
|---|---|---|---|---|---|---|---|---|---|---|---|---|---|---|---|---|
| | 205a | 205b | 205c | 205d | 205e | 205f | 205g | 205h | 205i | 205j | 205k | 205l | 205m | 205n | 205o | 205p |
| SW306(1,1,1,1) | Vref | Vref | Vref | Vref | Vsca | Vsca | Vsca | Vsca | Vsca | Vsca | Vsca | Vsca | Vsca | Vsca | Vsca | Vsca |
| SW306(1,1,1,0) | Vsca | Vref | Vref | Vref | Vref | Vsca | Vsca | Vsca | Vsca | Vsca | Vsca | Vsca | Vsca | Vsca | Vsca | Vsca |
| SW306(1,1,0,1) | Vsca | Vsca | Vref | Vref | Vref | Vref | Vsca | Vsca | Vsca | Vsca | Vsca | Vsca | Vsca | Vsca | Vsca | Vsca |
| SW306(1,1,0,0) | Vsca | Vsca | Vsca | Vref | Vref | Vref | Vref | Vsca | Vsca | Vsca | Vsca | Vsca | Vsca | Vsca | Vsca | Vsca |
| SW306(1,0,1,1) | Vsca | Vsca | Vsca | Vsca | Vref | Vref | Vref | Vref | Vsca | Vsca | Vsca | Vsca | Vsca | Vsca | Vsca | Vsca |
| SW306(1,0,1,0) | Vsca | Vsca | Vsca | Vsca | Vsca | Vref | Vref | Vref | Vref | Vsca | Vsca | Vsca | Vsca | Vsca | Vsca | Vsca |
| SW306(1,0,0,1) | Vsca | Vsca | Vsca | Vsca | Vsca | Vsca | Vref | Vref | Vref | Vref | Vsca | Vsca | Vsca | Vsca | Vsca | Vsca |
| SW306(1,0,0,0) | Vsca | Vsca | Vsca | Vsca | Vsca | Vsca | Vsca | Vref | Vref | Vref | Vref | Vsca | Vsca | Vsca | Vsca | Vsca |
| SW306(0,1,1,1) | Vsca | Vsca | Vsca | Vsca | Vsca | Vsca | Vsca | Vsca | Vref | Vref | Vref | Vref | Vsca | Vsca | Vsca | Vsca |
| SW306(0,1,1,0) | Vsca | Vsca | Vsca | Vsca | Vsca | Vsca | Vsca | Vsca | Vsca | Vref | Vref | Vref | Vref | Vsca | Vsca | Vsca |
| SW306(0,1,0,1) | Vsca | Vsca | Vsca | Vsca | Vsca | Vsca | Vsca | Vsca | Vsca | Vsca | Vref | Vref | Vref | Vref | Vsca | Vsca |
| SW306(0,1,0,0) | Vsca | Vsca | Vsca | Vsca | Vsca | Vsca | Vsca | Vsca | Vsca | Vsca | Vsca | Vref | Vref | Vref | Vref | Vsca |
| SW306(0,0,1,1) | Vsca | Vsca | Vsca | Vsca | Vsca | Vsca | Vsca | Vsca | Vsca | Vsca | Vsca | Vsca | Vref | Vref | Vref | Vref |
| SW306(0,0,1,0) | Vsca | Vsca | Vsca | Vsca | Vsca | Vsca | Vsca | Vsca | Vsca | Vsca | Vsca | Vsca | Vsca | Vref | Vref | Vref |
| SW306(0,0,1,1) | Vsca | Vsca | Vsca | Vsca | Vsca | Vsca | Vsca | Vsca | Vsca | Vsca | Vsca | Vsca | Vsca | Vsca | Vref | Vref |

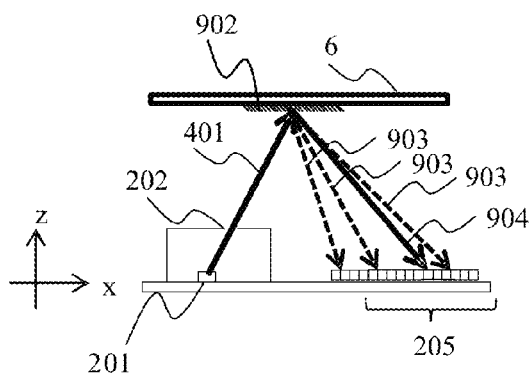
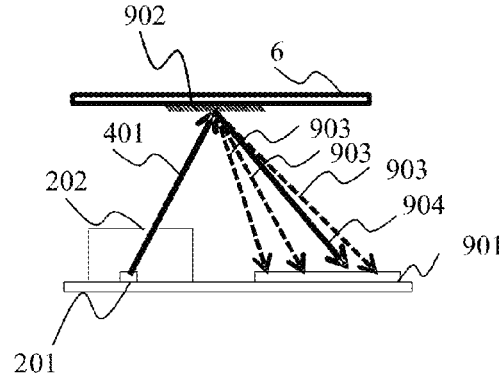
FIG. 9A      FIG. 9B
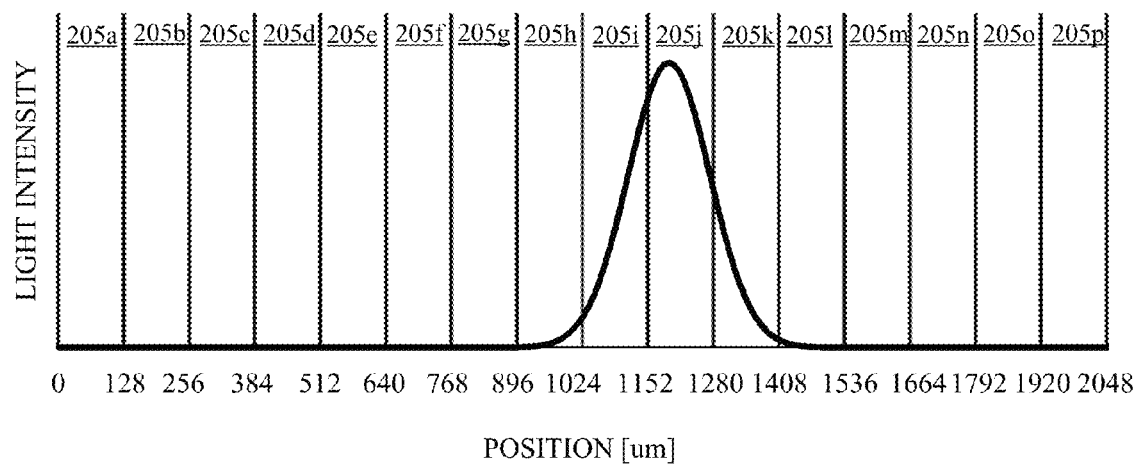
FIG. 9C

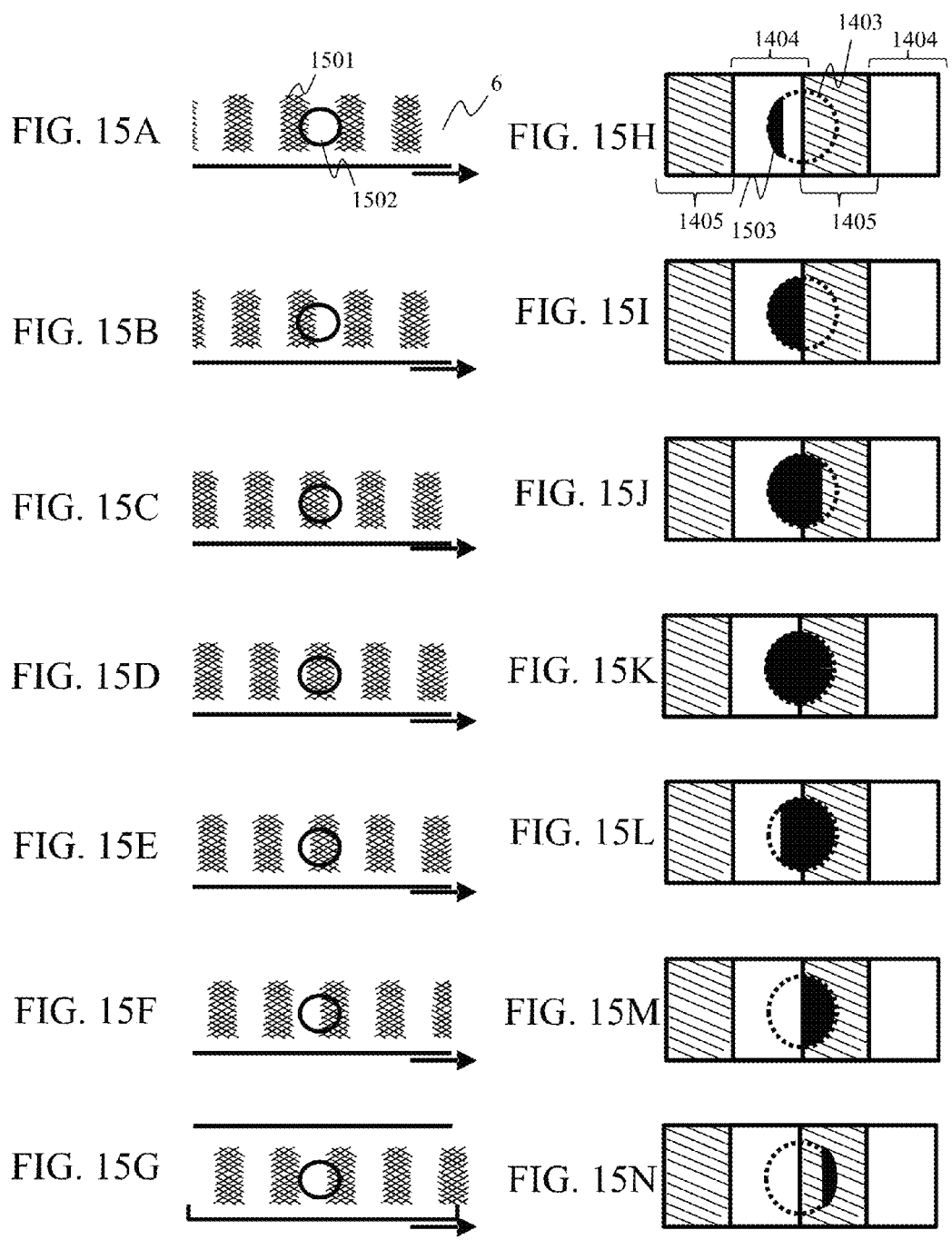

$V \propto \Delta T = \text{Average}(T_{1612}, T_{1611}) - \text{Average}(T_{1601}, T_{1602})$

| REGION SETTING INFORMATION (3bit) | OUTPUT TERMINAL CONNECTED WITH PHOTODIODES | | | | | | | | | | | | | | | |
|---|---|---|---|---|---|---|---|---|---|---|---|---|---|---|---|---|
| | 205a | 205b | 205c | 205d | 205e | 205f | 205g | 205h | 205i | 205j | 205k | 205l | 205m | 205n | 205o | 205p |
| SW306(1,1,1) | Va | Va | Va | Va | Vb | Vb | Vb | Vb | Va | Va | Va | Va | Vb | Vb | Vb | Vb |
| SW306(1,1,0) | NC | Vb | Va | NC | NC | Vb | Va | NC | NC | Vb | Va | NC | NC | Vb | Va | NC |
| SW306(1,0,1) | Vb | Va | Va | Va | Va | NC | Vb | Vb | Vb | NC | Va | Va | Va | Vb | Vb | NC |
| SW306(1,0,0) | NC | NC | Vb | Va | NC | NC | Vb | Va | NC | NC | Vb | Va | NC | NC | Vb | NC |
| SW306(0,1,1) | Vb | Vb | Va | Va | Va | Va | Va | Vb | Vb | Vb | Vb | NC | Va | Va | Vb | Vb |
| SW306(0,1,0) | NC | NC | NC | Vb | Va | Va | NC | Vb | Va | Vb | Vb | Va | NC | NC | Va | NC |
| SW306(0,0,1) | Vb | Vb | Vb | Va | Va | Va | Va | NC | Vb | Vb | Vb | NC | Va | Va | Va | Vb |
| SW306(0,0,0) | NC | NC | NC | NC | Vb | Va | NC | NC | Vb | Va | NC | NC | Vb | Va | NC | NC |

FIG. 18A

FIG. 18H
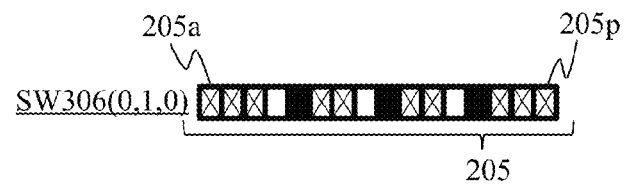
FIG. 18I
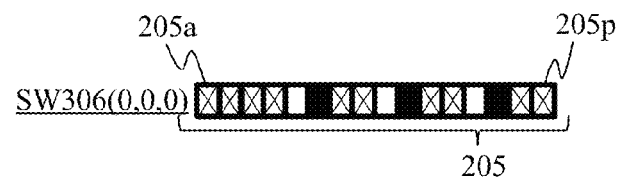
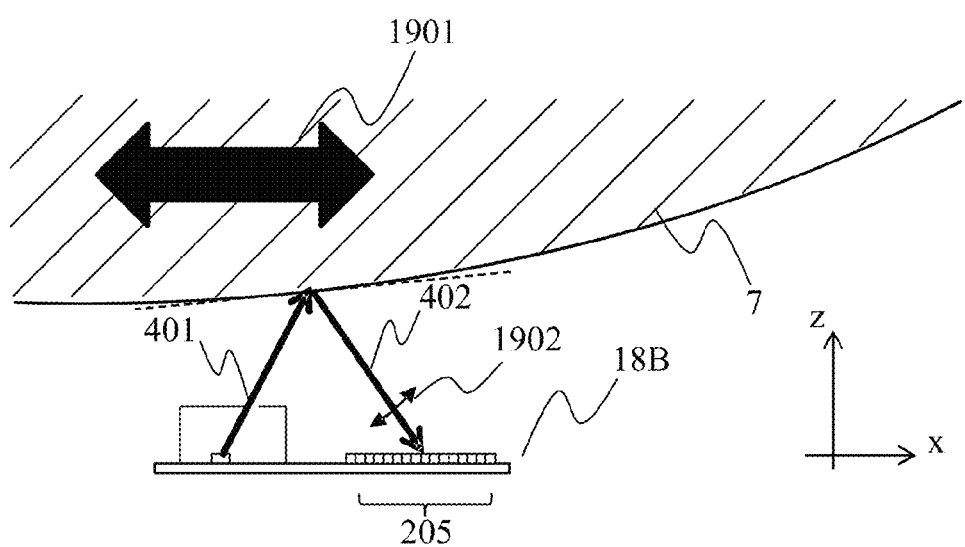
FIG. 19A

REFLECTION DETECTION APPARATUS AND APPARATUS USING THE SAME

BACKGROUND OF THE INVENTION

1. Field of the Invention

The present invention relates to a reflection detection apparatus that detects a reflected light from an object and that is suitable for detection of a color shift and a density in a color image forming apparatus such as a color laser printer or a color copier.

2. Description of the Related Art

Of the above-described color image forming apparatuses, a tandem-type image forming apparatus provided with photoreceptors for multiple colors, for example, forms a pattern on an intermediate transfer belt and detects, by using a light-receiving sensor (reflection sensor), a reflected light from the pattern to perform detection of the color shift and density as described below.

In the color shift detection, the tandem-type image forming apparatus uses a color shift detection-purpose image composed of a reference color pattern in which portions of a reference color are cyclically formed and a comparison color pattern in which portions of a comparison color are formed between the reference color portions. The apparatus detects a time at which each color pattern passes above the reflection sensor in response to changes in light amount of a specularly reflected light which is generated by the passage of each color pattern and calculates, from a result of the detection, a color shift amount of the comparison color with respect to the reference color.

On the other hand, in the density detection, the apparatus uses a density-inspection-purpose image (dither pattern) constituted by a toner image expressed by area coverage modulation. The apparatus detects, by the reflection sensor, a light amount of the specularly reflected light from a surface of the intermediate transfer belt on which the toner image is not formed and calculates the density by using a decrease amount of the light amount of the specularly reflected light from the surface of the intermediate transfer belt on which a toner image is formed depending on a tone corresponding to a result of the detection.

In this process, a diffusely reflected light from the toner mixes with the specularly reflected light, which causes an error in detected value of the light amount of the specularly reflected light. For this reason, subtracting a detected light amount of only the diffusely reflected light from a detected light amount of a total reflected light, namely, the mixture of the specularly and diffusely reflected lights enables extracting only the light amount of the specularly reflected light, which enables calculating an exact density. However, in the specularly reflected light from the intermediate transfer belt, a ray fluctuation is generated corresponding to a relative angle that depends on a relative alignment relation between the intermediate transfer belt and the reflection sensor. A large ray fluctuation causes the reflection sensor to erroneously detect the specularly reflected light when only the light amount of the diffusely reflected light is to be detected. This erroneous detection consequently makes it impossible to detect an exact light amount of only the specularly reflected light, namely, the density.

Japanese Patent Laid-Open No. 02-256076 discloses a reflection sensor having a light-receiving region whose area is increased so as to prevent the specularly reflected light from reaching outside of a light-receiving region of the reflection sensor even if the ray fluctuation is generated.

However, such an increase in light-receiving region area for the specularly reflected light like the reflection sensor disclosed in Japanese Patent Laid-Open No. 02-256076 results in an increase in light amount of the diffusely reflected light reaching the light-receiving region from toner. This increase in the light amount of the diffusely reflected light reaching the light-receiving region increases, in density detection, the light amount of the diffusely reflected light compared to that of the specularly reflected light which decreases with an increase of the density, which makes it impossible to acquire, from the reflection sensor, a density detection signal with a sufficient amplitude corresponding to the light amount if the specularly reflected light. In this case, the light amount of the specularly reflected light from the surface of the intermediate transfer belt on which the toner image is not formed, the light amount being a reference for the density, contains an imaging noise component due to reflectance unevenness on the surface and to minute concavities and convexities caused in manufacturing of the intermediate transfer belt. For this reason, a decrease in amplitude of the density detection signal decreases an S/N ratio of the density detection signal.

SUMMARY OF THE INVENTION

The present invention provides a reflection detection apparatus capable of accurately detecting a light amount of a specularly reflected light without an area of a light-receiving region being increased even if a ray fluctuation of the specularly reflected light is generated. The present invention further provides an apparatus using the reflection detection apparatus.

The present invention provides as an aspect thereof a reflection detection apparatus including multiple light-receiving elements configured to detect a pattern formed on an object by receiving a reflected light from the object, and a selector configured to select a first light-receiving element group from the multiple light-receiving elements. The selector is configured to select the first light-receiving element group that includes one or more light-receiving elements each mainly receiving a specularly reflected light from an area of the object where no pattern is formed among the multiple light-receiving elements, on a basis of outputs from the multiple light-receiving elements, and the detection of the pattern is made on a basis of an output from the first light-receiving element group.

The present invention provides as another aspect thereof an apparatus including the above reflection detection apparatus, and an operation portion configured to operate by using an output from the reflection detection apparatus.

The present invention provides as still another aspect thereof an image forming apparatus including the above reflection detection apparatus, a transfer body on which a latent image to which toner is adhered is formed, and a detector configured to detect, by using an output from the reflection detection apparatus, at least one of a density of the toner, a color shift of the toner, a moving speed of the transfer body and a variation in slope of the transfer body.

Further features of the present invention will become apparent from the following description of exemplary embodiments with reference to the attached drawings.

BRIEF DESCRIPTION OF THE DRAWINGS

FIG. 1 is a block diagram illustrating a configuration of an image forming apparatus using a color shift/density detection apparatus of each embodiment of the present invention.

FIG. 7 illustrates connection between light-receiving elements of the color shift/density sensor and output terminals selected by the switch circuit in Embodiment 1.

FIGS. 9A to 9E illustrate an effect provided by an area difference of detection regions for a specularly reflected light in Embodiment 1.

FIGS. 15A to 15N illustrate a patch on an intermediate transfer belt and a projected image on a light-receiving surface in Embodiment 2.

FIGS. 18A to 18I illustrate detection regions of the color shift/density sensor in Embodiment 3.

FIGS. 19A to 19C illustrate a variation in slope of a surface detected by a color shift/density detection apparatus that is Embodiment 4 of the present invention.

DESCRIPTION OF THE EMBODIMENTS

Figure 2:
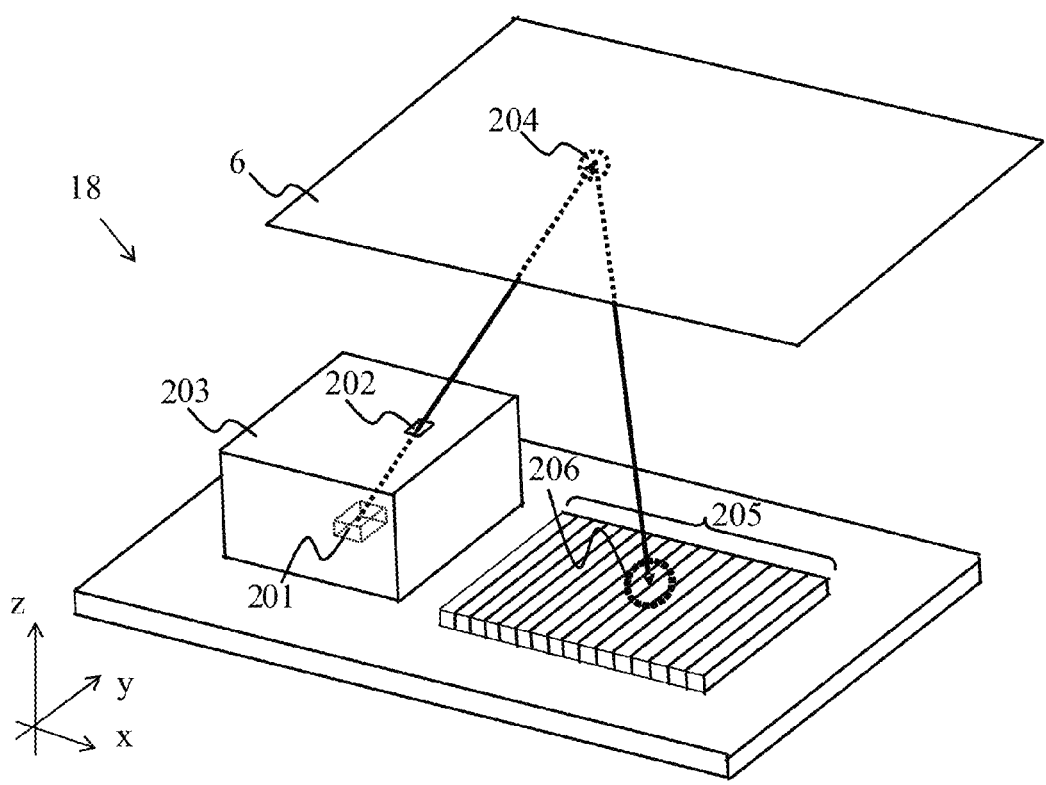
FIG. 2 illustrates a configuration of a color shift/density sensor in the color shift/density detection apparatus that is Embodiment 1 of the present invention.

Exemplary embodiments of the present invention will be described below with reference to the attached drawings.

First, description will be made of a color image forming apparatus that is an apparatus using a color shift/density detection apparatus as a reflection detection apparatus of each of embodiments described later, with reference to FIG. 1.

In FIG. 1, constituent elements denoted by reference numerals that end with "Y", "M", "C" or "Bk" correspond to yellow, magenta, cyan or black which are colors of developers (toners). However, in the following description, symbols Y, M, C and Bk are omitted for constituent elements common to these colors.

The color image forming apparatus is provided with a charging unit 1, a photosensitive drum 2, an exposing unit 3, a developing unit 4 and a primary transfer roller 5 for each of the toner colors: yellow, magenta, cyan and black. The charging unit 1 electrically charges the photosensitive drum 2, which is an image supporting body rotatable in a direction indicated by a thin arrow in the drawing. The exposure unit 3 projects a laser light onto the photosensitive drum 2 to form thereon an electrostatic latent image. The developing unit 4 applies a developing bias to the photosensitive drum 2 and supplies toner to the electrostatic latent image to develop the electrostatic latent image into a toner image that is a visible image. The primary transfer roller 5 applies a primary transfer bias to the photosensitive drum 2 to transfer the toner image formed thereon onto an intermediate transfer belt 6.

The intermediate transfer belt 6 as a transfer body is rotationally driven (transported) by driving rollers 7 in a direction (X direction) indicated by a thick arrow. The toner images are transferred, onto a surface (object), from the photosensitive drums 2 for the respective toner colors such that the toner images overlap one another, which results in formation of a color image on the intermediate transfer belt 6.

Transporting rollers 8, 9 and 10 transport a recording material in a cassette 20 along a transporting path 11 to a secondary transfer roller 12. The secondary transfer roller 12 applies a secondary transfer bias to the intermediate transfer belt 6 to transfer the toner images mutually overlapping on the intermediate transfer belt 6 to the recording material. A residual toner not transferred to the recording material and thus remaining on the intermediate transfer belt 6 is removed by a cleaning blade 13 and then collected by a waste toner collection container 14.

The recording material to which the toner image is transferred is heated and pressurized by a fuser 15. The recording material to which the toner image is fixed thereby is let out by a transporting roller 16 outside the apparatus.

An engine controller 17 includes a micro controller installed therein and performs sequence controls of various actuators (not illustrated), various controls using sensors and others in the image forming apparatus.

At a position facing the intermediate transfer belt 6 (position with a gap from the intermediate transfer belt 6 in a Z direction in the drawing), a color shift/density sensor 18 of each embodiment described later is provided.

A first embodiment (Embodiment 1) will describe a configuration of the color shift/density detection apparatus including the color shift/density sensor 18, a method of selecting a light-receiving element group to be used for detecting a specularly reflected light amount, a method of detecting a color shift amount and a method of detecting a density in this order.

On the other hand, a second embodiment will describe a method of detecting a color shift and a density utilizing a 180-degree phase difference arrangement of light-receiving elements of the color shift/density sensor 18, and a third embodiment (Embodiment 3) will describe a method of detecting a moving speed of the intermediate transfer belt 6.

Furthermore, a fourth embodiment (Embodiment 4) will describe a method of detecting a variation in slope angle of the surface of a detection object (intermediate transfer belt 6) utilizing the 180-degree phase difference arrangement of the light-receiving elements.

Finally, a fifth embodiment (Embodiment 5) will describe an optical structure that suppresses an amount of a ray fluctuation due to a slope of a surface of a detection object to shorten required lengths of multiple light-receiving elements.

Embodiment 1

FIG. 2 illustrates a configuration of a color shift/density sensor (reflection sensor) 18 as a sensor head of the color shift/density detection apparatus that is Embodiment 1 of the present invention. The color shift/density sensor 18 includes an infrared-wavelength light source 201, an aperture member 203 having an aperture 202 that limits a width of a light spot 204 projected from the light source 201 onto an intermediate transfer belt 6 and multiple light-receiving elements 205 each capable of receiving light (reflected light) reflected by the intermediate transfer belt 6.

The multiple light-receiving elements 205 are arranged in line in an x direction in FIG. 2 so as to form a line sensor. The x direction is a main direction in which the light emitted from the light source 201 proceeds while passing through and exiting from the aperture 202 and then being reflected by a portion 204 of the surface of the intermediate transfer belt 6. In this embodiment, the x direction corresponds to the X direction illustrated in FIG. 1, namely, a direction in which the intermediate transfer belt 6 is moved (transported). The x direction is hereinafter also referred to as "a transporting direction". In this embodiment, a width direction orthogonal to the transporting direction of the intermediate transfer belt 6 is defined as a y direction, and a direction from the color shift/density sensor 18 toward the intermediate transfer belt 6 (i.e., a direction orthogonal to the x and y directions) is defined as a z direction corresponding to the Z direction in FIG. 1.

Figure 3A:
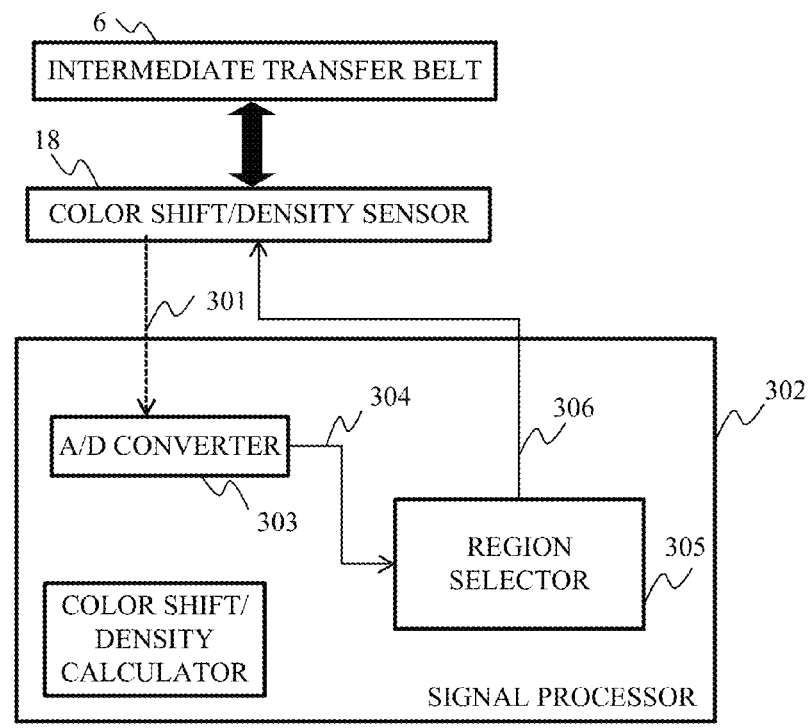
FIGS. 3A and 3B are block diagrams illustrating a configuration of the color shift/density detection apparatus of Embodiment 1.
Figure 3B:
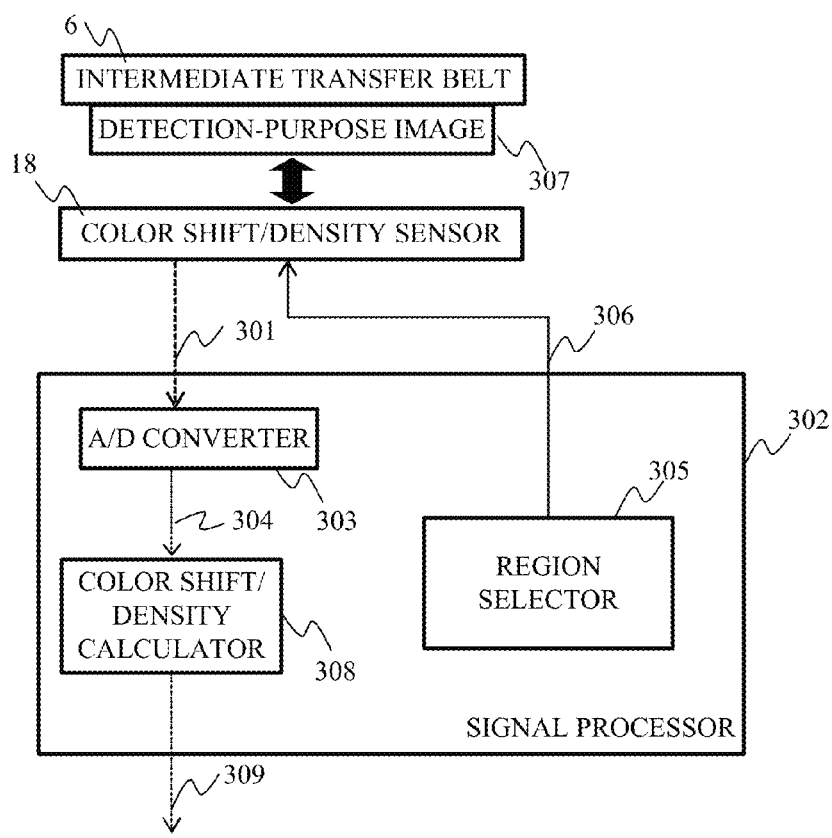

FIGS. 3A and 3B illustrate the configuration of the color shift/density detection apparatus including the color shift/density sensor (hereinafter simply referred to as "a sensor") 18. FIG. 3A illustrates an operation of the color shift/density detection apparatus performed to select (set) a specular reflection detection region. In FIG. 3A, a region selector 305 as a selector outputs, to the sensor 18, region setting information 306 used to divide the light-receiving elements 205 for setting multiple light-receiving element groups. Each of the light-receiving element groups is constituted by two or more light-receiving element.

The sensor 18 (light-receiving elements 205) receives and photoelectrically converts a specularly reflected light from the intermediate transfer belt 6 and outputs a resulting analog voltage value 301 corresponding to a light amount detected by the light-receiving elements 205 to a signal processor 302. An A/D converter 303 of the signal processor 302 digitalizes the analog voltage value 301 to produce detected light amount information 304 and outputs this information to the region selector 305.

The region selector 305 selects from the multiple light-receiving element group, depending on the detected light amount information acquired from the output of each of the light-receiving element groups set in the sensor 18, a first light-receiving element group serving as the specular reflection detection region and a second light-receiving element group serving as a diffuse reflection detection region. The first light-receiving element group is a light-receiving element group that mainly receives the specularly reflected light from the intermediate transfer belt 6 more than a diffusely reflected light therefrom. On the other hand, the second light-receiving element group is a light-receiving element group that mainly receives the diffusely reflected light more than the specularly reflected light from the intermediate transfer belt 6. In this embodiment, in a state where no toner image being formed on the intermediate transfer belt 6, the region selector 305 selects one of the multiple light-receiving element groups whose detected light amount is largest as the first light-receiving element group and selects the others as the second light-receiving element group. That is, in this embodiment, the second light-receiving element group is selected so as to have a wider light-receiving area than that of the first light-receiving element group.

FIG. 3B illustrates an operation of the color shift/density detection apparatus performed in a state where a color shift/density detection-purpose image (hereinafter simply referred to as "a detection-purpose image") 307 that is a toner image used for color shift/density detection and formed on the surface of the intermediate transfer belt 6 facing the sensor 18. The region selector 305 first outputs, to the sensor 18, the region setting information 306 to be used for setting the first and second light-receiving element groups selected as illustrated in the state of FIG. 3A. This output causes the sensor 18 to set the first and second light-receiving element groups, which are the specular reflection and diffuse reflection detection regions, respectively.

The sensor 18 photoelectrically converts, by the first light-receiving element group, the specularly reflected light from the detection-purpose image 307 on the intermediate transfer belt 6 and outputs the analog voltage value 301 corresponding to the light amount detected by the first light-receiving element group to the signal processor 302. The A/D converter 303 of the signal processor 302 digitalizes the analog voltage value 301 to produce the detected light amount information 304 and outputs this information to the color shift/density calculator 308. The color shift/density calculator 308 serving as a specular reflection calculator and a pattern interval calculator performs a calculation by using the detected light amount information 304 to produce color shift/density information 309 and sends this information to an engine controller 17 of the image forming apparatus, which is illustrated in FIG. 1, as feedback information for image formation.

Description will now be made of a method of variably selecting the first light-receiving element group of the sensor 18 so that the specularly reflected light can be detected even if a ray fluctuation is generated.

Figure 4A:
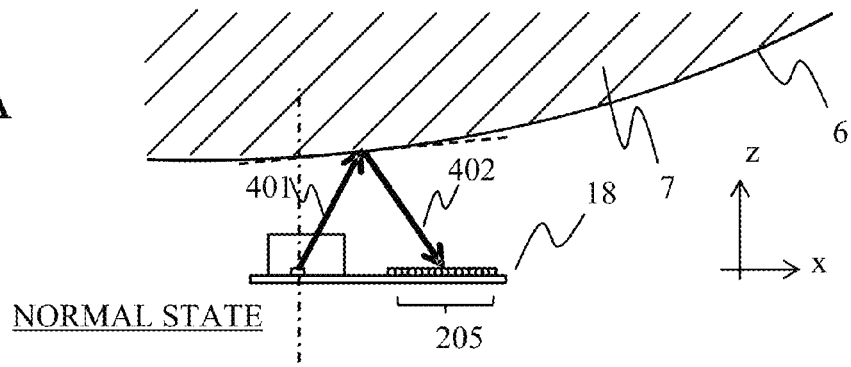
FIGS. 4A to 4D illustrate an example in which a ray fluctuation is generated in Embodiment 1.

First, with reference to FIGS. 4A to 4D, description will be made of an example of the ray fluctuation. FIG. 4A illustrates a state (hereinafter referred to as "a normal state") in which the sensor 18 of the image forming apparatus illustrated in FIG. 1 is fixed at a normal position at a normal angle. The sensor 18 is disposed so as to face a surface (hereinafter referred to as "a belt curved surface") of a curved surface portion of the intermediate transfer belt 6 along a roller surface of the driving roller 7 around which the intermediate transfer belt 6 is wound. In the normal state, a specularly reflected ray 402 from the belt curved surface enters a center of the light-receiving elements 205 in the direction (X direction) in which the light-receiving elements 205 are arranged in line.

Figure 4B:
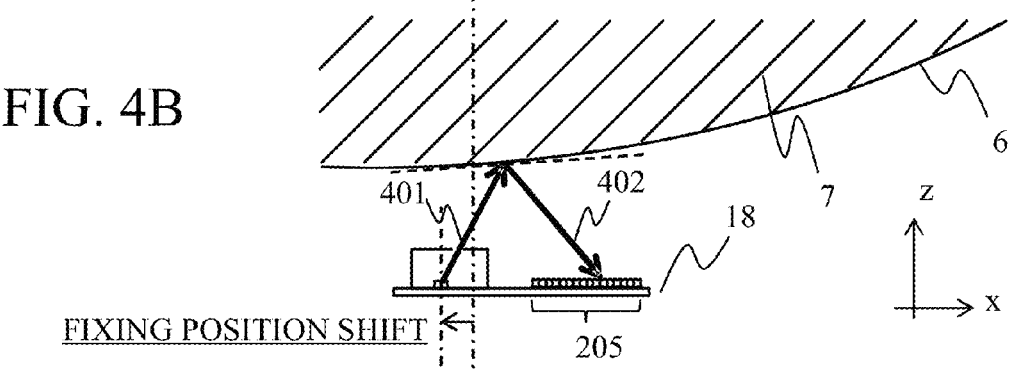

FIG. 4B illustrates a case where a fixing position of the sensor 18 is shifted in the X direction from the normal position illustrated in FIG. 4A. The positional shift of the sensor 18 in the X direction changes an incident position on the belt curved surface at which a ray 401 from the sensor 18 hits. This change in the incident position changes a reflection direction of the specularly reflected ray 402, causing the ray fluctuation. As a result, an entrance position of the specularly reflected ray 402 on the light-receiving elements 205 is shifted in the X direction from the center of the light-receiving elements 205 depending on a direction and an amount of the ray fluctuation.

Figure 4C:
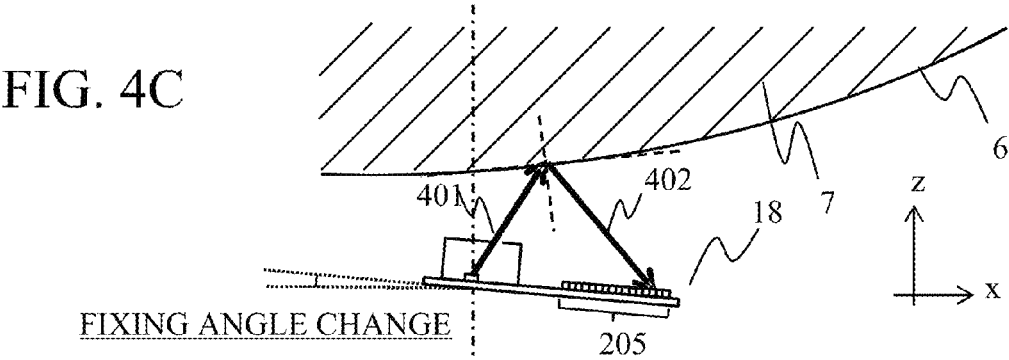

FIG. 4C illustrates a case where a fixing angle of the sensor 18 changes from the normal angle illustrated in FIG. 4A. The change in the fixing angle changes an incident angle of the ray 401 from the sensor 18 to the belt curved surface and the incident position thereof on the belt curved surface. This change in the incident angle and position changes the reflection direction of the specularly reflected ray 402, causing the ray fluctuation. As a result, the entrance position of the specularly reflected ray 402 on the light-receiving elements 205 is shifted in the X direction depending on the direction and the amount of the ray fluctuation.

Figure 4D:
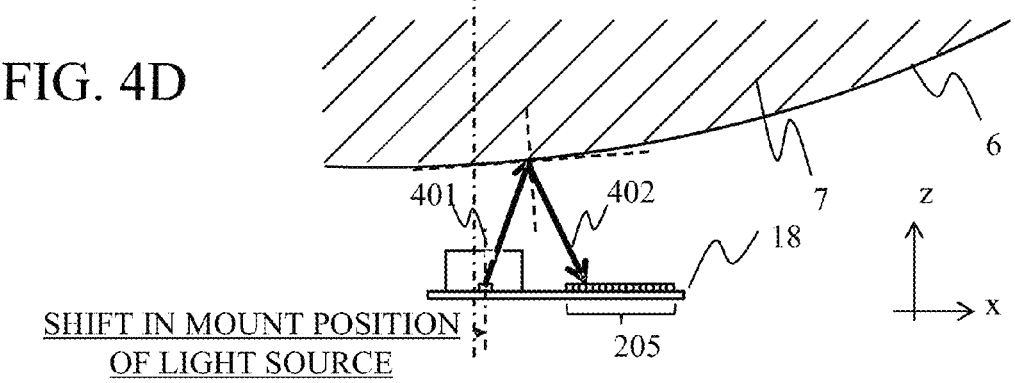

FIG. 4D illustrates a case where a mount position at which the light source 201 is mounted in the sensor 18 is shifted from a proper position. In this case, depending on a positional relation between the light source 201 and the aperture 202, the incident position and angle of the ray 401 on and to the belt curved surface changes, which changes the reflection direction of the specularly reflected ray 402 and thereby causes the ray fluctuation. As a result, the entrance position of the specularly reflected ray 402 on the light-receiving elements 205 is shifted in the X direction depending on the direction and the amount of the ray fluctuation.

FIGS. 5A to 5D each illustrate a light-receiving element group 501 where the specularly reflected ray (a flux of rays having a certain width in the X direction) 402 enters from the belt curved surface in a corresponding one of the states illustrated in FIGS. 4A to 4D. In addition, in each of FIGS. 5A to 5D, a light intensity distribution of the specularly reflected ray 402 on the light-receiving element group 501 is shown above the light-receiving element group 501.

As shown in FIGS. 4A to 4D and 4A to 5D, the fixing position and angle of the sensor 18 with respect to the intermediate transfer belt 6, the shift in the mount position of the light source inside the sensor 18 and the like cause the ray fluctuation of the specularly reflected ray, which consequently shifts the position at which the specularly reflected ray enters the light-receiving elements 205.

Next, with reference to FIGS. 6 and 7 and 8A to 8M, description will be made of a method of selecting (setting) the first light-receiving element group, which is the specular reflection detection region, from the multiple light-receiving elements 205.

Figure 5A:
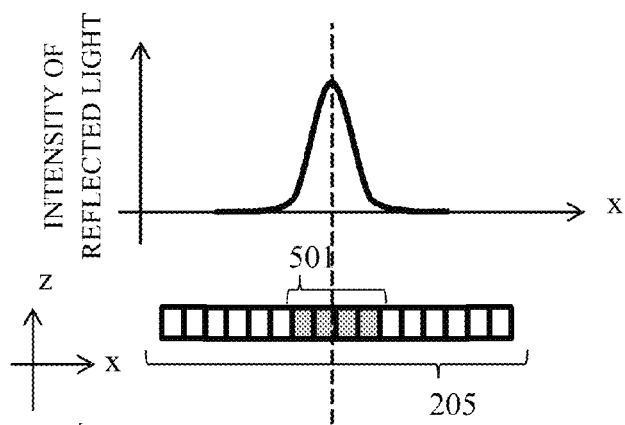
FIGS. 5A to 5D illustrate a light intensity distribution on the color shift/density sensor corresponding to the ray fluctuation in Embodiment 1.
Figure 5B:
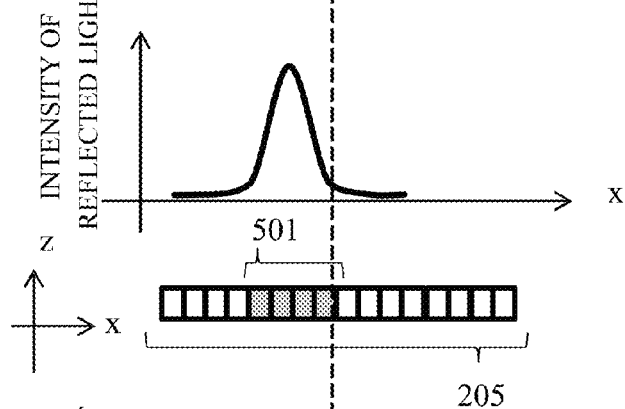
Figure 5C:
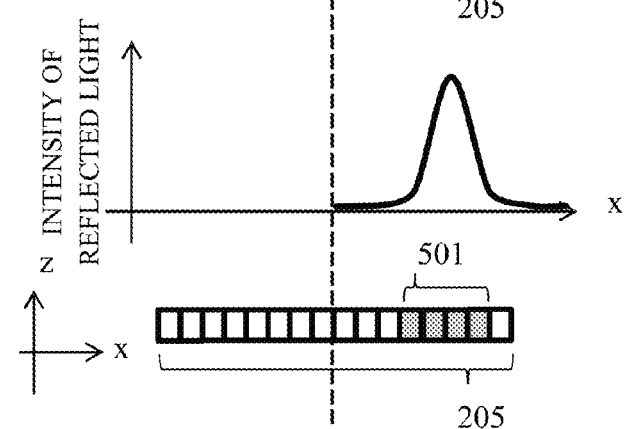
Figure 5D:
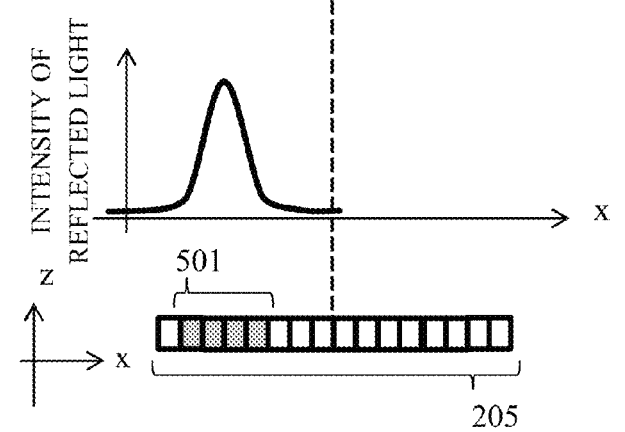
Figure 6:
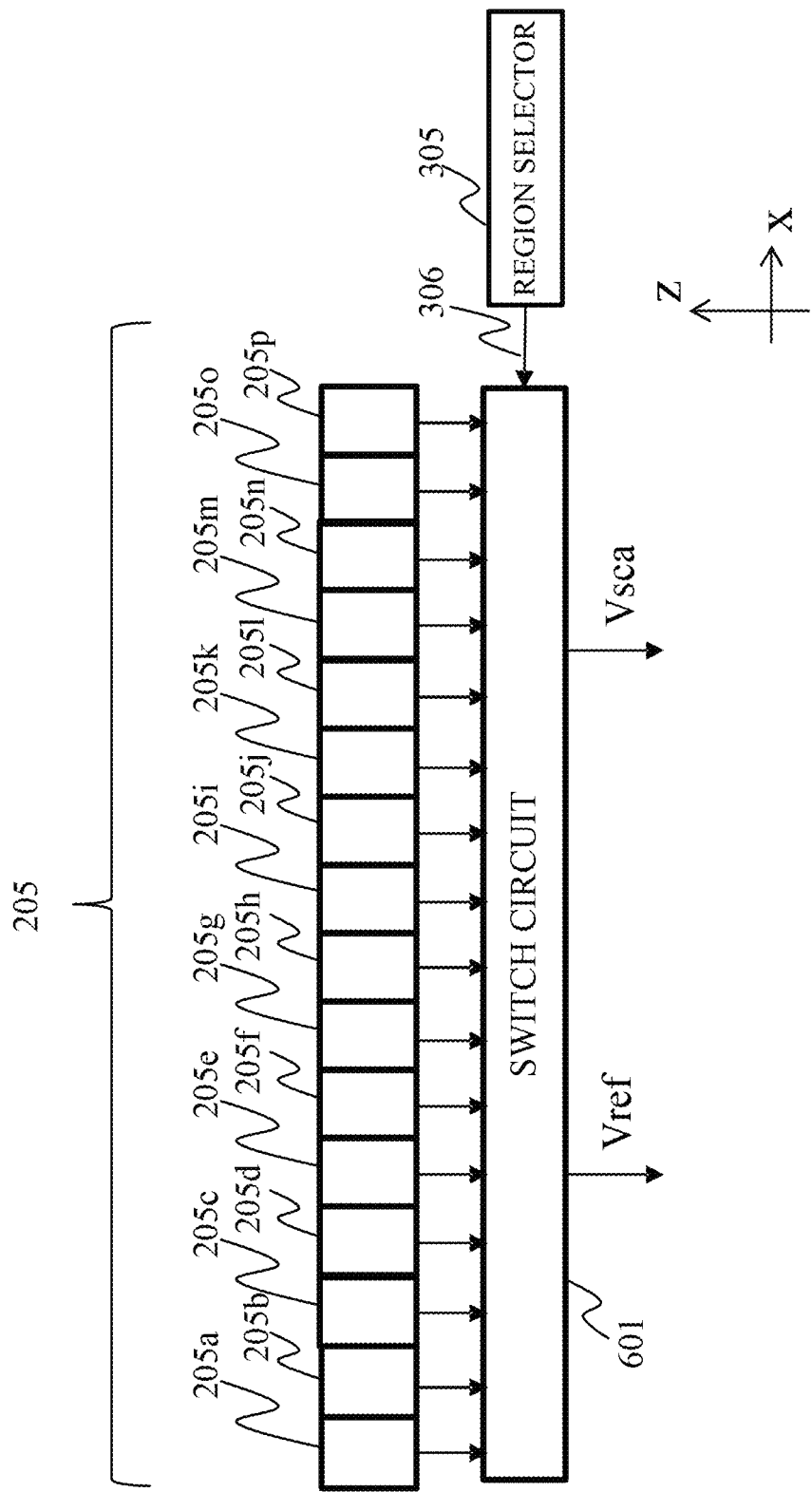
FIG. 6 illustrates a switch circuit provided for the color shift/density sensor in Embodiment 1.

FIG. 6 illustrates a switch circuit that switches a light-receiving element group referenced by the sensor 18, that is, a light-receiving element group to be subjected to a determination of whether or not to select that group as the first light-receiving element group. The selected light-receiving group is hereinafter referred to respectively as "a referenced element group". Individual light-receiving elements 205a to 205p included in the light-receiving elements 205 are connected to the switch circuit 601, and their output signals are selectively connected to output terminals $V_{ref}$ and $V_{sca}$ by the switch circuit 601 depending on the region setting information 306 from the region selector 305. Detected voltages of the light-receiving elements (four light-receiving elements illustrated in each of FIGS. 5A to 5D in this embodiment) selected as elements of the referenced element group are summed, and the summed voltage is output as a detected voltage $V_{ref}$. On the other hand, detected voltages of the other light-receiving elements are summed, and the summed voltage is output as a detected voltage $V_{sca}$.

FIG. 7 illustrates output terminals $V_{ref}$ and $V_{sca}$ to which output signals of the light-receiving elements are selectively connected depending on the region setting information 306. In this embodiment, the region setting information 306 is a 4-bit signal. For instance, a row indicated by symbol SW306 (1,1,1,1) in the drawing shows that, when the region setting information 306 is a 4-bit signal whose all bits are high level, the output signals of the light-receiving elements 205a to 205d of the referenced element group are connected to the output terminal $V_{ref}$ and the output signals of the light-receiving elements 205e to 205p are connected to the output terminal $V_{sca}$. In this manner, the referenced element group is switched depending on the 4-bit signal (hereinafter referred to as "a switching signal") as the region setting information 306.

Figure 8A:
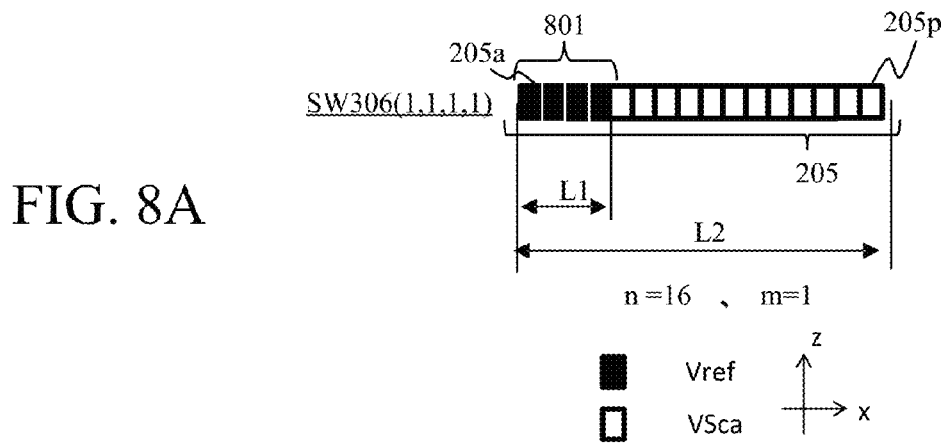
FIGS. 8A to 8M illustrate relations between various region setting information for the color shift/density sensor and detection regions of the sensor in Embodiment 1.
Figure 8B:
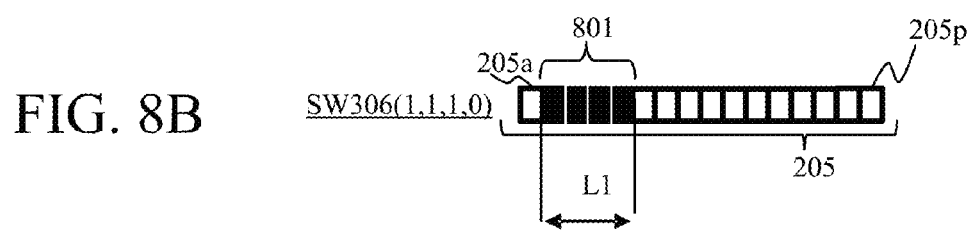
Figure 8C:
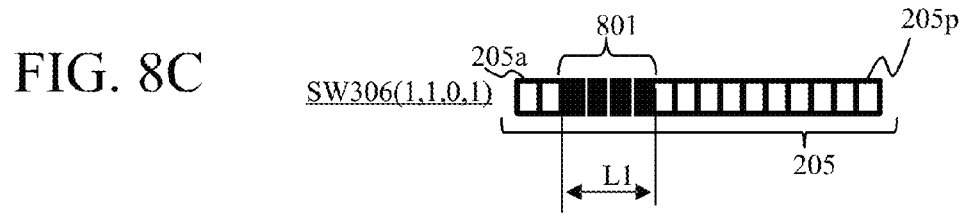
Figure 8D:
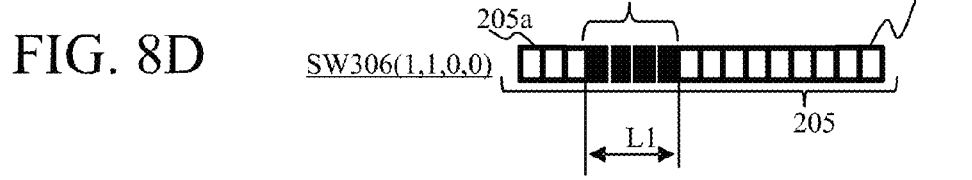
Figure 8E:
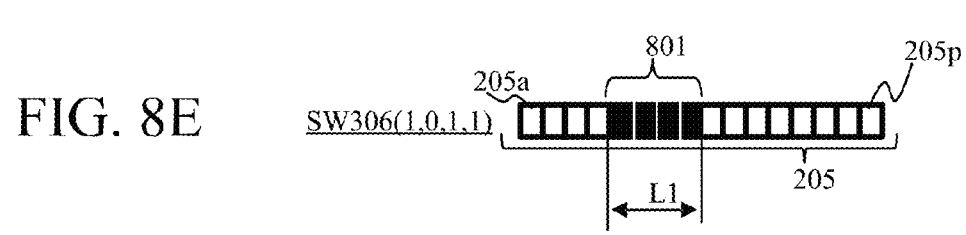
Figure 8F:
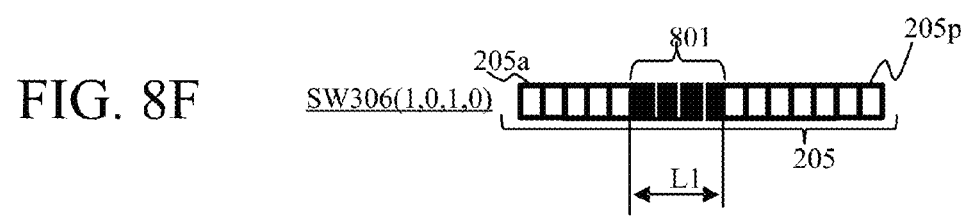

FIGS. 8A to 8M illustrate sequential switching of a referenced element group 801 in response to changes of the switching signal. For instance, FIG. 8A illustrates, in black, among the 16 light-receiving elements 205a to 205p, the referenced element group 801 constituted by the four light-receiving elements 205a to 205d selected corresponding to the 4-bit switching signal SW306(1,1,1,1) illustrated in FIG. 7.

In this embodiment, an entire light-receiving region of the sensor 18 is formed by the 16 light-receiving elements 205a to 205p arranged in line in the X direction such that the entire light-receiving region has a length (entire length of the light-receiving region) of L2. The entire light-receiving region with the length of L2 is divided into n=16 small regions (light-receiving elements) in the X direction. The referenced element group 801 with the length of L1 constituted by four of the 16 light-receiving elements is shifted on an element-by-element basis (m=1) in response to the switching signal (region setting information 306) while maintaining the length of L1. In this manner, the region selector 305 sequentially shifts a first number (n/4=4 in this embodiment) of the light-receiving elements mutually adjacent in the X direction in units of light-receiving elements whose number is a second number (m=1 in this embodiment) equal to or less than the first number and thereby sets multiple (13) referenced element groups 801. Then, the region selector 305 selects, as the first light-receiving element group serving as the specular reflection detection region, one of the multiple referenced element groups 801 which provides a highest detected voltage $V_{ref}$.

Figure 8G:
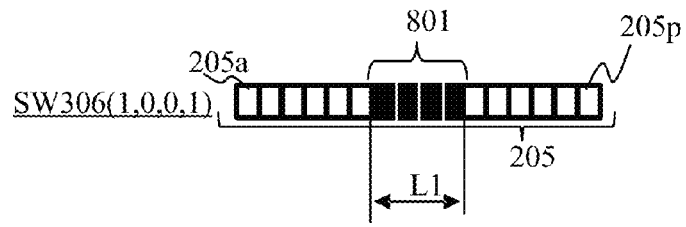

Description will be made of a relation between the states illustrated in FIGS. 5A to 5D and the referenced element group 801 selected as the specular reflection detection region. In the normal state illustrated in FIG. 5A, the detected voltage value $V_{ref}$ of the selected referenced element group 801 selected at a center of the entire light-receiving region as illustrated in FIG. 8G becomes highest. Thereby, this referenced element group 801 is selected as the specular reflection detection region. In a ray fluctuation state illustrated in FIG. 5B, the detected voltage value $V_{ref}$ of the referenced element group 801 shifted from the center depending on a direction and an amount of the ray fluctuation as illustrated, for example, in FIG. 8E becomes highest. Thereby, this referenced element group 801 is selected as the specular reflection detection region. Similarly, in ray fluctuation states illustrated in FIGS. 5C and 5D, the detected voltage value $V_{ref}$ of the referenced element group 801 shifted from the center as respectively illustrated, for example, in FIGS. 8L and 8B becomes highest. Thereby, one of these referenced element group 801 is selected as the specular reflection detection region.

As described above, setting the referenced element group 801 whose detected voltage value $V_{ref}$ becomes highest depending on the direction and amount of the ray fluctuation as the specular reflection detection region enables detecting the light amount of the specularly reflected light with good accuracy without an expansion of the specular reflection detection region itself regardless of generation of the ray fluctuation in the specularly reflected light.

Next, description will be made of an effect provided when the light-receiving region (whose entire length is L2) of the sensor 18 is formed by the multiple light-receiving elements 205 as illustrated in FIG. 9A (that is, as in this embodiment) by comparison with an effect provided when the light-receiving region is formed by a single light-receiving element 901 having an entire light-receiving region length identical to the entire length L2 as illustrated in FIG. 9B. In the following description, Condition 1 refers to forming the light-receiving region of the sensor 18 divided by the multiple light-receiving elements 205, and Condition 2 refers to forming the light-receiving region by the single light-receiving element 901.

The entire length L2 of the light-receiving elements 205 and of the single light-receiving element 901 is sufficiently long so that a specularly reflected light 904 from the intermediate transfer belt 6 does not reach outside of the light-receiving region even if the ray fluctuation is generated due to the shift of the fixing position shift and the change of the fixing angle of the sensor 18 with respect to the intermediate transfer belt 6. For instance, in a case where a size of the projected light spot on the intermediate transfer belt 6 is Φ=0.2 mm, a size of the reflected light spot on the light-receiving elements 205 is approximately 0.5 to 0.6 mm, the entire length L2 of the light-receiving region is 2.41 mm. In this case, a width of each of the 16 light-receiving elements in the x direction in Condition 1 (FIG. 9A) is 0.15 mm.

Figure 8H:
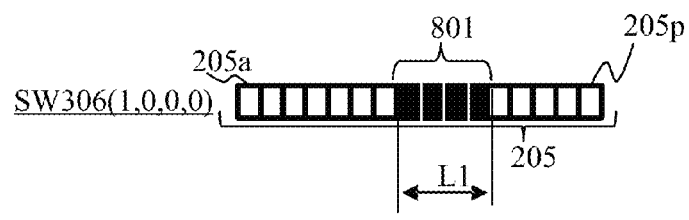
Figure 8I:
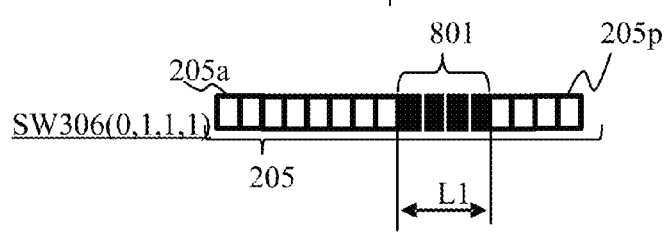
Figure 8J:
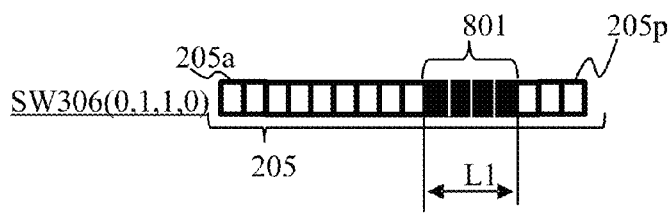
Figure 8K:
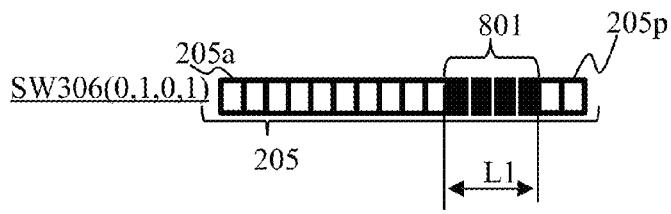
Figure 8L:
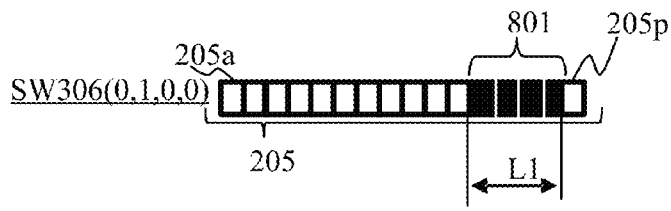
Figure 8M:
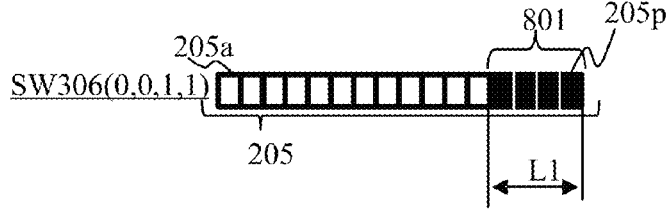

FIG. 9C illustrates an intensity distribution of the specularly reflected light on the entire light-receiving region in a state in which the detection-purpose image is not formed on the intermediate transfer belt 6. This intensity distribution has an intensity peak formed by the specularly reflected light 904 whose center is at a light-receiving position corresponding to a position of the light-receiving element 205j in Condition 1. In this state, in Condition 1, the referenced element group illustrated in FIG. 8H is selected as the specular reflection detection region.

Figure 9D:
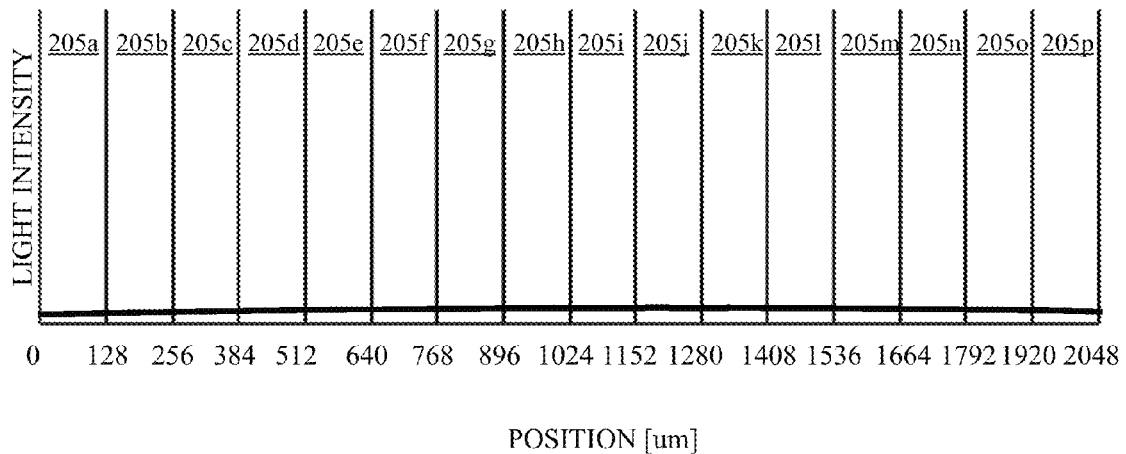

FIG. 9D illustrates an intensity distribution of the specularly reflected light 904 on the entire light-receiving region in a state in which the detection-purpose image is formed on the intermediate transfer belt 6. In this state, a diffusely reflected light 903 from the detection-purpose image approximately uniformly reaches the entire light-receiving region.

Figure 9E:
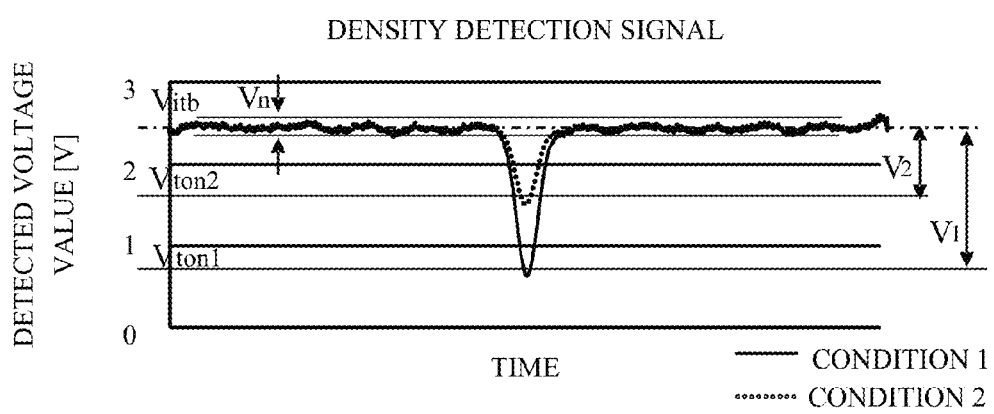

FIG. 9E illustrates, with time, detected voltage values of density detection signals provided in Conditions 1 and 2 when the intensity distributions of the specularly reflected light and the diffusely reflected light respectively illustrated in FIGS. 9C and 9D are formed on the light-receiving region.

Symbol $V_{itb}$ represents an average value of the density detection signal corresponding to the intensity of the specularly reflected light from the intermediate transfer belt 6. The density detection signal corresponding to the intensity of the specularly reflected light contains an amplitude fluctuation Vn as a noise component due to a reflectance variation of the surface of the intermediate transfer belt 6 and minute concavities and convexities on the surface. This applies to both Conditions 1 and 2.

On the other hand, the diffusely reflected lights from the detection-purpose image on the intermediate transfer belt 6 in Conditions 1 and 2 have a difference in detected light amounts due to a difference in light-receiving areas of regions where the reflected lights are received. In Condition 1, the diffuse reflection detection region (second light-receiving element group) other than the specular reflection detection region (first light-receiving element group) receives the diffusely reflected light from the detection-purpose image. This means that the light-receiving area in Condition 1 is smaller than that in Condition 2. For this reason, in Condition 1, a voltage value $V_{ton1}$ of the density detection signal provided from the diffuse reflection detection region is lower (in other words, the density is thicker) as compared to that in Condition 2, and an amplitude V1 is larger than that in Condition 2. In contrast thereto, in Condition 2 in which the light-receiving area of the diffusely reflected light from the detection-purpose image is larger than that in Condition 1, a voltage value $V_{ton2}$ of the density detection signal is higher than $V_{ton1}$ (in other words, the density is thinner), and only a smaller amplitude V2 than V1 is provided.

Comparison in S/N ratios between V1 and V2 provides a relation of V1/Vn>V2/Vn. This comparison result shows that Condition 1, that is, variably selecting the specular reflection detection region in the light-receiving region as in this embodiment, in further other words, separating the specular reflection detection region from the diffuse reflection detection region enables improving the S/N ratio of the density detection signal.

Although this embodiment described the case where all part of the entire light-receiving region other than the specular reflection detection region is selected as the diffuse reflection detection region, only part of the light-receiving region other than the specular reflection detection region may be selected as the diffuse reflection detection region.

Figure 10A:
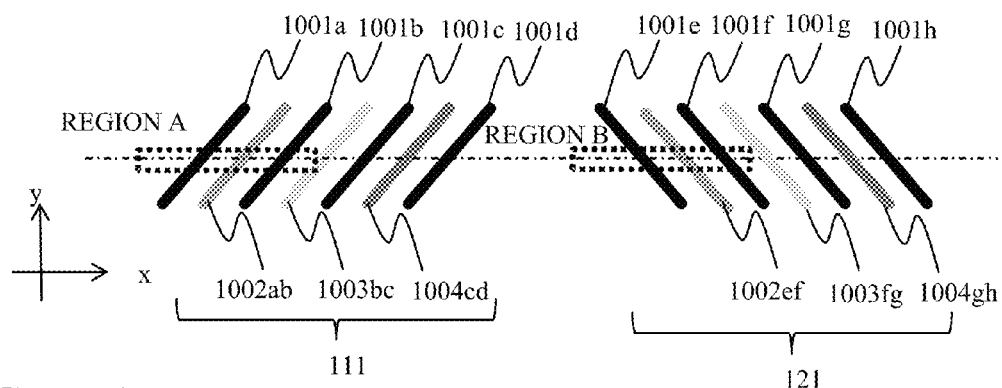
FIGS. 10A to 10D illustrate a color shift detection method in Embodiment 1.

Next, description will be made of a method of detecting the color shift with reference to FIGS. 10A to 10D. FIG. 10A illustrates the detection-purpose image as the toner image that is formed on the intermediate transfer belt 6 and is to be used for the color shift detection. For the detection-purpose image to be used for the color shift detection, two toner patch groups 111 and 121 tilted mutually oppositely in the X direction are arranged tandemly in the X direction. Each toner patch group includes reference color toner patches (Bk) 1001 disposed at 0 (360)-degree phase positions in the X direction and having a maximum density, and comparison color toner patches(Y) 1002, (M) 1003 and (C) 1004 disposed one by one at 180-degree phase positions between the reference color toner patches. In the drawings, reference letters a to h are respectively added after reference numeral 1001 of the reference color toner patches in order in the X direction, and reference numerals 1002, 1003 and 1004 of the comparison color toner patches(Y), (M) and (C) are followed by the reference letters of the reference color toner patches disposed across each comparison color toner patch. For instance, the comparison color toner patch(Y) 1002ab is disposed between the reference color toner patches 1001a and 1001b. On the other hand, the comparison color toner patch(M) 1003fg is disposed between the reference color toner patches 1001f and 1001g.

The sensor 18 sequentially detects times at which multiple patterns composed of the color toner patches formed on the intermediate transfer belt 6 pass through a position where a light spot is formed by the light from the light source 201. Thereafter, the sensor 18 calculates, from the detected passage times, a positional shift of each comparison color toner patch with respect to the reference color toner patch adjacent thereto (that is, a distance between the reference color toner patch and the comparison color toner patch).

Figure 10B:
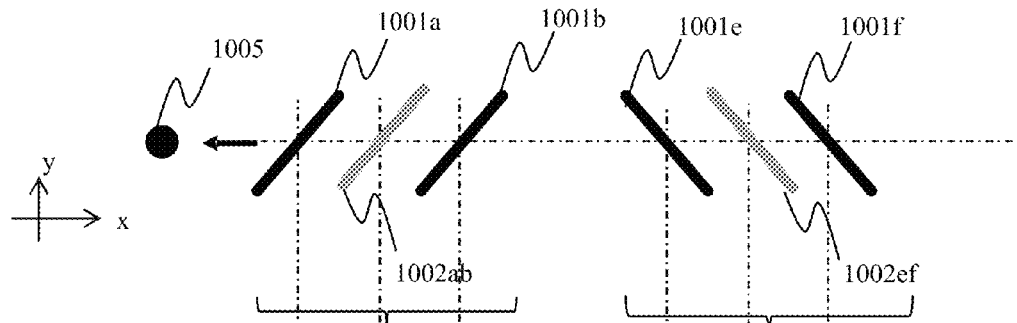

Next, description will be made of a method of detecting the passage time of each toner patch. FIG. 10B illustrates partial toner patch groups 1011 and 1021 included in regions A and B respectively set for the two toner patch groups 111 and 121 in FIG. 10A. The partial toner patch group 1011 includes the reference color toner patches 1001a and 1001b and the comparison color toner patch(Y) 1002ab disposed therebetween. On the other hand, the partial toner patch group 1021 includes the reference color toner patches 1001e and 1001f and the comparison color toner patch(Y) 1002ef disposed therebetween. These toner patches are transported by the drive of the intermediate transfer belt 6 in a direction indicated by an arrow in the drawing and respectively pass through the position (hereinafter referred to as "a spot position") 1005 at which the light spot is formed by the light from the sensor 18.

Figure 10C:
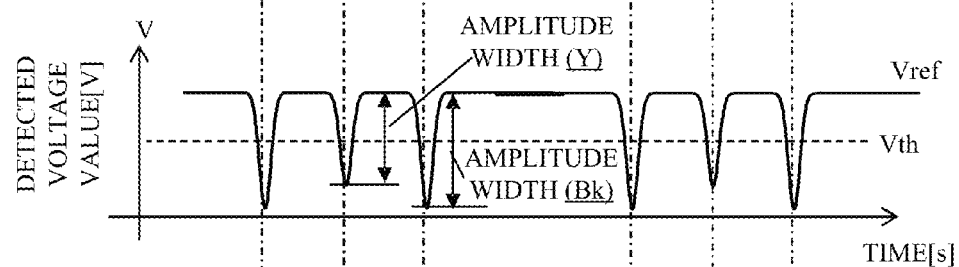

FIG. 10C illustrates a voltage value (detected voltage value) $V_{ref}$ of a color shift detection signal output from the specular reflection detection region of the sensor 18 in response to the passage of each toner patch through the spot position 1005 illustrated in FIG. 10B. When no toner patch passes through the spot position 1005, the light amount of the specularly reflected light from the intermediate transfer belt 6 is large, and therefore the voltage value $V_{ref}$ is high. When the reference color toner patch passes through the spot position 1005, the light amount of the specularly reflected light from the intermediate transfer belt 6 is smallest and the light amount of the diffusely reflected light is also small due to light absorption by that reference color toner patch. Consequently, the voltage value $V_{ref}$ is approximately zero, and therefore a voltage amplitude value of the color shift detection signal is increased.

On the other hand, the comparison color toner patches(Y) 1002ab and 1002ef are formed by light-reflective toner. Since a typical toner patch is formed by toner particles whose particle diameter is several micrometers, the toner patch has a surface with concavities and convexities and thus has light diffusivity as an optical property. The light amount of the diffusely reflected light received by the light-receiving element varies depending on a relation in size between the light-receiving element, the comparison color toner patch and the light spot, and the voltage value $V_{ref}$ of the color shift detection signal does not become zero. For this reason, the voltage amplitude value of the color shift detection signal is smaller as compared to when the reference color toner patch passes through the spot position 1005.

Figure 10D:
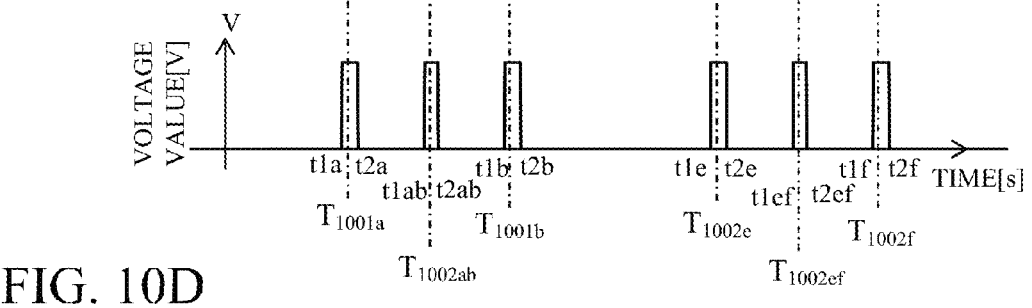

FIG. 10D illustrates a variation with time of the voltage value $V_{ref}$ of the color shift detection signal from the sensor 18 input to the signal processor 302 and then binarized by the A/D converter 303 with a threshold voltage $V_{th}$. The passage time at which each toner patch passes through the spot position 1005 is an average value of times at which two polarity changes of the binary signal are detected. Employing such an average passage time enables calculating, without an influence of the difference in the voltage amplitude value of the color shift detection signal caused by a difference in color among the toner patches, a time at which a center of each toner patch passes through the spot position 1005. When the times at which the two polarity changes of the binary signal with respect to the reference color toner patch 1001a are detected are $t_{1a}$ and $t_{2a}$, the passage time of the reference color toner patch 1001a is calculated by following expression (1):

$$T_{1001a} = \frac{(t_{1a} + t_{2a})}{2} \quad (1)$$

Similarly, times at which the other toner patches 1002ab, 1002ef, 1001e, 1002ef and 1001f included in the partial toner patch groups 1011 and 1021 pass through the spot position 1005 are expressed by following expressions (2) to (6). Times $t_{1ab}$, $t_{2ab}$; $t_{1b}$, $t_{2b}$; $t_{1e}$, $t_{2e}$; $t_{1ef}$, $t_{2ef}$; and $t_{1f}$, $t_{2f}$ represent times at which the two polarity changes of the binary signal with respect to the toner patches 1002ab, 1002ef, 1001e, 1002ef and 1001f are detected.

$$T_{1002ab} = \frac{(t_{1ab} + t_{2ab})}{2} \quad (2)$$

$$T_{1001b} = \frac{(t_{1b} + t_{2b})}{2} \quad (3)$$

$$T_{1001e} = \frac{(t_{1e} + t_{2e})}{2} \quad (4)$$

$$T_{1001ef} = \frac{(t_{1ef} + t_{2ef})}{2} \quad (5)$$

$$T_{1001f} = \frac{(t_{1f} + t_{2f})}{2} \quad (6)$$

Next, description will be made of a method of calculating the color shift. In the following description, the method of calculating the color shift of yellow (Y) with respect to the reference color (Bk) will be shown.

As the color shift, a sub-scan directional color shift that is a color shift in the transporting direction (X direction) of the intermediate transfer belt 6 and a main scan directional color shift that is a color shift in a direction (Y direction) orthogonal to the transporting direction are generated. Following expressions (7) to (12) are used for calculation of the main scan directional color shift and the sub-scan directional color shift.

$$\text{SUB-SCAN DIRECTIONAL COLOR SHIFT} = \frac{(a-b)-(c-d)}{4} \quad (7)$$

$$\text{MAIN SCAN DIRECTIONAL COLOR SHIFT} = \frac{(a-b)+(c-d)}{4} \quad (8)$$

$$a = T_{1002ab} - T_{1001a} \quad (9)$$

$$b = T_{1001b} - T_{1002ab} \quad (10)$$

$$c = T_{1001ef} - T_{1002e} \quad (11)$$

$$d = T_{1001f} - T_{1002ef} \quad (12)$$

When the color shift is generated, a time difference $\Delta T_Y$ is calculated from expression (7) or (8) and sent to the engine controller 17. The engine controller 17 corrects, depending on the time difference $\Delta T_Y$, the color shift in yellow with respect to the reference color Bk by, for example, correcting an exposure timing at the exposing unit 3Y to adjust a transfer position.

Although this embodiment described the detection and the correction of the color shift in yellow that is one of the comparison colors to the reference color, the color shifts in cyan and magenta can also be detected and corrected by the same process as that described above. Therefore, description of the detection and the correction of the color shifts in cyan and magenta is omitted.

Although this embodiment described the case where only the specular reflection detection region is used in the color shift detection, a process to subtract an output corresponding to the diffusely reflected light from the output from the specular reflection detection region may alternatively be performed to suppress a decrease in amplitude caused by the reflective toner patch. Moreover, only the diffuse reflection detection region may be used for the color shift detection for the toner patch color having diffusive reflectivity.

Next, with reference to FIGS. 11A to 11D, description will be made of a method of detecting the density. In this embodiment, the detection-purpose image to be used for the density detection is an image with a dither pattern expressing densities with a minimum unit of 4×4 dots, 1 dot that is a minimum unit of the detection-purpose image having a size of 42.3 μm×42.3 μm.

Figure 11A:
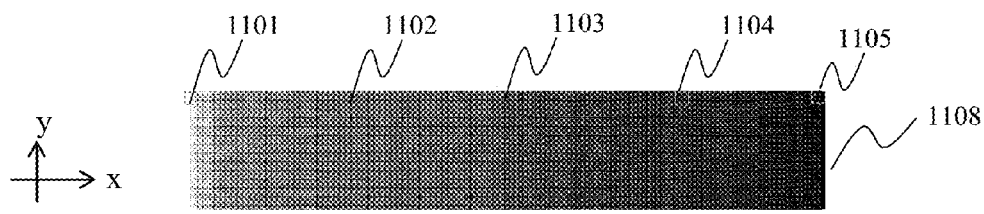
FIGS. 11A to 11D illustrate a density detection method in Embodiment 1.

FIG. 11A illustrates a graduation pattern 1108 to be used as the detection-purpose image. Local densities of the graduation pattern 1108 are expressed by the above-described minute dither pattern.

Figure 11B:
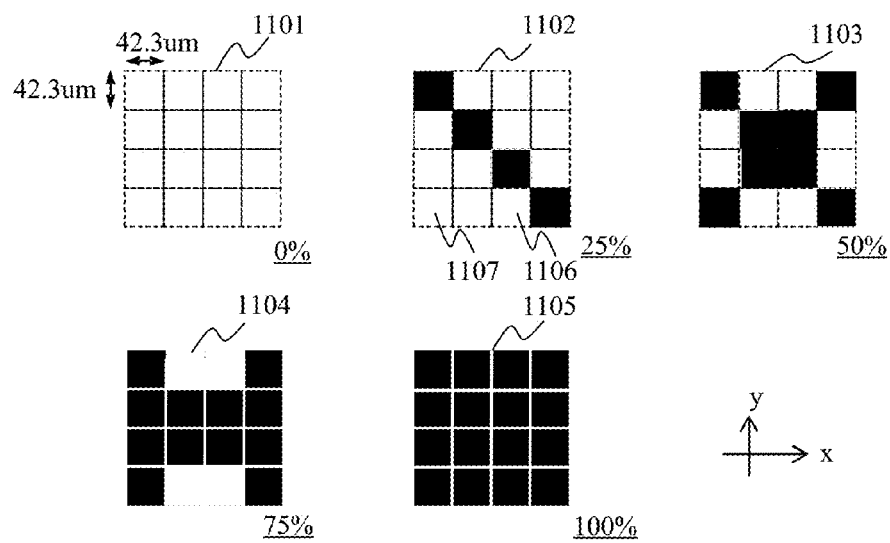

FIG. 11B illustrates dither patterns in a 0% density region 1101, a 25% density region 1102, a 50% density region 1103, a 75% density region 1104 and a 100% density region 1105 of the graduation pattern (toner pattern) 1108. Frame lines in each density region illustrated in the drawing are shown for clearly showing each dot and therefore are not actually present. A black portion of the dither pattern indicates, on the surface of the intermediate transfer belt 6a, a toner accumulation portion 1106 on which the toner accumulates (is adhered). On the other hand, a white portion of the dither pattern indicates a region where the toner is not present, that is, an exposed portion (hereinafter referred to as "an exposed surface portion") 1107 of the surface of the intermediate transfer belt 6.

A change in density of the density region changes an area of the exposed surface portion 1107 of the intermediate transfer belt 6, which results in a change in area of a region in the dither pattern which specularly reflects an incident light and also results in a change in area of the toner accumulation portion 1106. Since color of the toner changes a light reflectance of the toner, this embodiment employs a method of calculating the density of the toner by using as an index an increase or a decrease in specularly reflected light amount which is independent of properties of the toner.

Figure 11C:
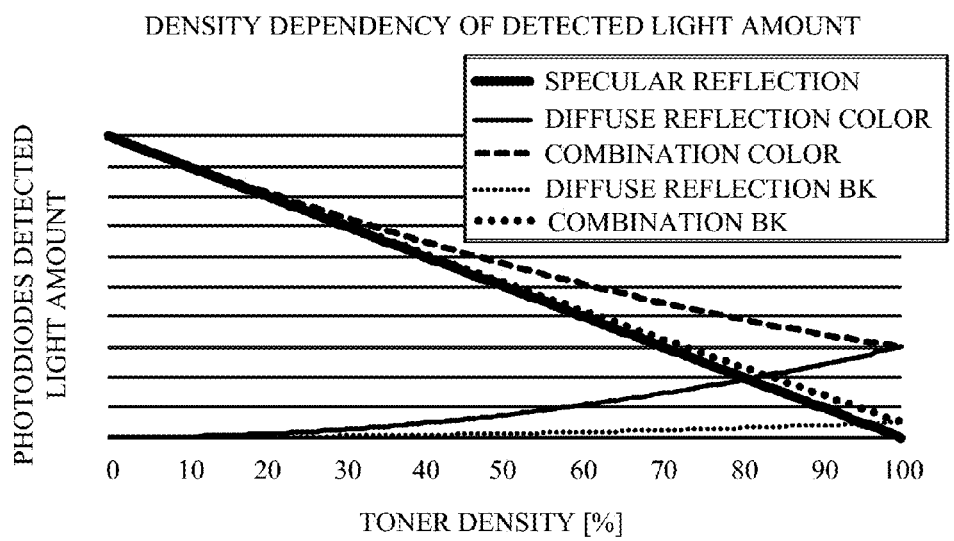

FIG. 11C illustrates toner density dependencies of the specularly reflected light amount and the diffusely reflected light amount detected in the specular reflection detection region, which is the first light-receiving element group of the sensor 18. In the drawing, a vertical axis indicates the detected light amount, and a horizontal axis indicates the density. As to the specularly reflected light amount indicated by a thick solid line (specular reflection) in the drawing, as the density increases, the area of the exposed surface portion 1107 of the intermediate transfer belt 6 linearly decreases, so that the detected light amount linearly decreases corresponding thereto. As to the diffusely reflected light amounts respectively indicated by a thin dotted line (diffuse reflection BK) and a thin solid line (diffuse reflection Color) in the drawing, these light amounts change nonlinearly depending on the density; the detected light amounts have a difference due to a difference in spectral characteristics of a color toner and a black toner for a wavelength of the light source. For these reasons, each of the reflected light amounts detected in the specular reflection detection region has a property that, as indicated in the drawing by a thick dotted line (combination BK) and a dashed line (combination Color), nonlinearity of the diffusely reflected light appears with increasing the density. This property causes a density detection error for the diffusely reflected light amount in a medium-to-high density range. Therefore, in order to calculate the density, it is necessary to remove a component of the diffusely reflected light amount from a detected value of the light amount in the specular reflection detection region.

Figure 11D:
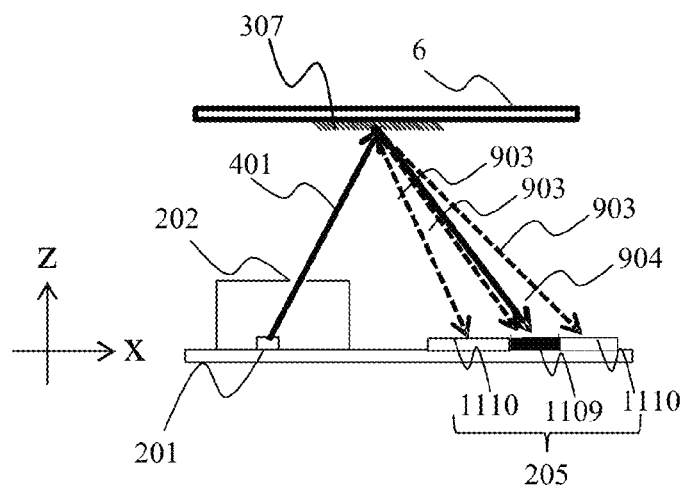

Next, description will be made of a method of removing the component of the diffusely reflected light amount from the detected light amount value in the specular reflection detection region of the sensor 18. FIG. 11D illustrates a side view of the sensor 18. Of the ray (light flux) 401 emitted from the light source 201, passing through the aperture 202 and then projected onto the detection-purpose image 307, the specularly reflected light 904 enters the specular reflection detection region 1109, which is the first light-receiving element group. Meanwhile, the diffusely reflected light 903 generated by the toner pattern 1108 of the detection-purpose image 307 also enters the specular reflection detection region 1109.

The specularly reflected light 904 does not enter a diffuse reflection detection region 1110, which is the second light-receiving element group and is adjacent to the specular reflection detection region 1109, but only the diffusely reflected light 903 enters that region 1110. Therefore, the color shift/density calculator 308 performs a calculation using following expression (13) to calculate a difference between a detected voltage value $V_{ref}$ corresponding to the detected light amount value in the specular reflection detection region 1109 where both the specularly reflected light 904 and the diffusely reflected light 903 enter and a detected voltage value $V_{sca}$ corresponding to the detected light amount in the diffuse reflection detection region 1110 where only the diffusely reflected light 903 enters. This calculation enables extracting a voltage value V corresponding only to the specularly reflected light amount. In other words, the color shift/density calculator 308 can calculate, by using the outputs ($V_{ref}$ and $V_{sca}$) from the first and second light-receiving element groups, an output component (V) corresponding to the specularly reflected light in the output from the first light-receiving element group.

$$V_{(SPECULAR\ REFLECTION)} = V_{ref(SPECULAR+DIFFUSE\ REFLECTIONS)} - V_{sca(DIFFUSE\ REFLECTION)} \quad (13)$$

However, when the specular reflection detection region 1109 and the diffuse reflection detection region 1110 between which the difference in the voltage values corresponding to their detected light amounts is calculated have a difference in detection sensitivity for the diffusely reflected light amount corresponding to an identical density, it is necessary to correct at least one of those voltage values.

For this reason, the color shift/density calculator 308 calculates, from a ratio between the detected voltage value $V_{ref}$ corresponding to the diffusely reflected light amount and the voltage value $V_{sca}$ corresponding to the diffusely reflected light amount in a state where the specularly reflected light is not present when a maximum density is detected, a correction coefficient α based on the detection sensitivity difference as expressed by following expression (14):

$$0_{(MAXIMUM\ DENSITY)} = V_{ref(DIFFUSE\ REFLECTION\ AT\ MAXIMUM\ DENSITY)} - \alpha \times V_{sca(DIFFUSE\ REFLECTION\ AT\ MAXIMUM\ DENSITY)} \quad (14)$$

In the density calculation, as expressed by following expression (15), the color shift/density calculator 308 subtracts a value acquired by multiplying the voltage value $V_{sca}$ in the diffuse reflection detection region by the correction coefficient α from the detected voltage value $V_{ref}$ in the specular reflection detection region. This calculation enables removing the component of the diffusely reflected light for which these detection regions have mutually different detection sensitivities.

$$V_{(SPECULAR\ REFLECTION)} = V_{ref(SPECULAR+DIFFUSE\ REFLECTIONS)} - \alpha \times V_{sca(DIFFUSE\ REFLECTION)} \quad (15)$$

The above-described method enables calculating, by performing the calculation using the detected light amount values (voltage values) in the specular reflection detection region (first light-receiving element group) and the diffuse reflection detection region (second light-receiving element group), only the specularly reflected light amount in the specular reflection detection region and thereby enables detecting the density with good accuracy.

As described above, this embodiment variably selects the specular reflection detection region to enable improving the S/N ratio of the density detection signal acquired from the specular reflection detection region. This improvement in S/N ratio makes it possible to reduce the detection error due to the diffusely reflected light undesirably entering the specular reflection detection region and thus to improve a detection accuracy for the specularly reflected light.

The number of the light-receiving elements provided in the light-receiving region of the sensor 18 and the setting of the multiple light-receiving element groups, both described above, are merely an example. For instance, the light-receiving region may alternatively be constituted by using a larger number of the light-receiving elements (that is, by dividing the light-receiving region into a larger number of the small regions). Furthermore, the multiple light-receiving element groups may alternatively be set by shifting the light-receiving element group in units of light-receiving elements whose number is another second number which is two or more, but equal to or less than the first number. These alternatives enable detecting the specularly reflected light with a higher accuracy and detecting the specularly reflected light in a shorter period of time.

Moreover, the diffuse reflection detection region may be set, in part of the multiple light-receiving elements other than the specular reflection detection region, as a region for detecting the diffusely reflected light amount equivalent to that in the specular reflection detection region. This setting enables omitting the process of calculating the correction coefficient α in the density detection.

Furthermore, when detecting a target that can be determined only by the detection of the diffusely reflected light amount such as density unevenness in a high-density toner patch, the diffusely reflected light amount may only be detected to make the determination.

Embodiment 2

Next, with reference to FIGS. 12A to 12C and 13A to 13F, description will be made of a color shift/density detection apparatus that is Embodiment 2 of the present invention. A color shift/density sensor (hereinafter simply referred to as "a sensor") 18A in the color shift/density detection apparatus of this embodiment sets two sets of light-receiving element groups having a 180-degree phase difference.

In this embodiment, the sensor 18A is capable of setting a specular reflection detection region and a diffuse reflection detection region to enable responding to a large ray fluctuation with a small number of input channels and also of detecting a transporting speed (moving speed) of the intermediate transfer belt 6. The detection of the transporting speed of the intermediate transfer belt 6 enables monitoring an operation status of the image forming apparatus and detecting a sudden speed variation of the intermediate transfer belt 6.

Figure 12A:
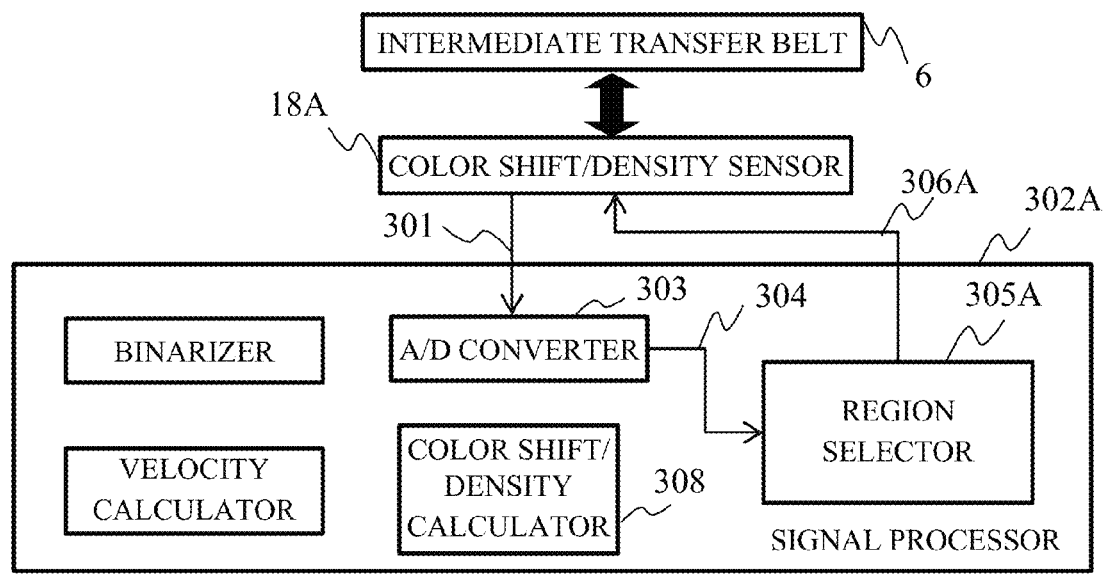
FIGS. 12A to 12C are block diagrams illustrating a configuration of a color shift/density detection apparatus that is Embodiment 2 of the present invention.
Figure 12B:
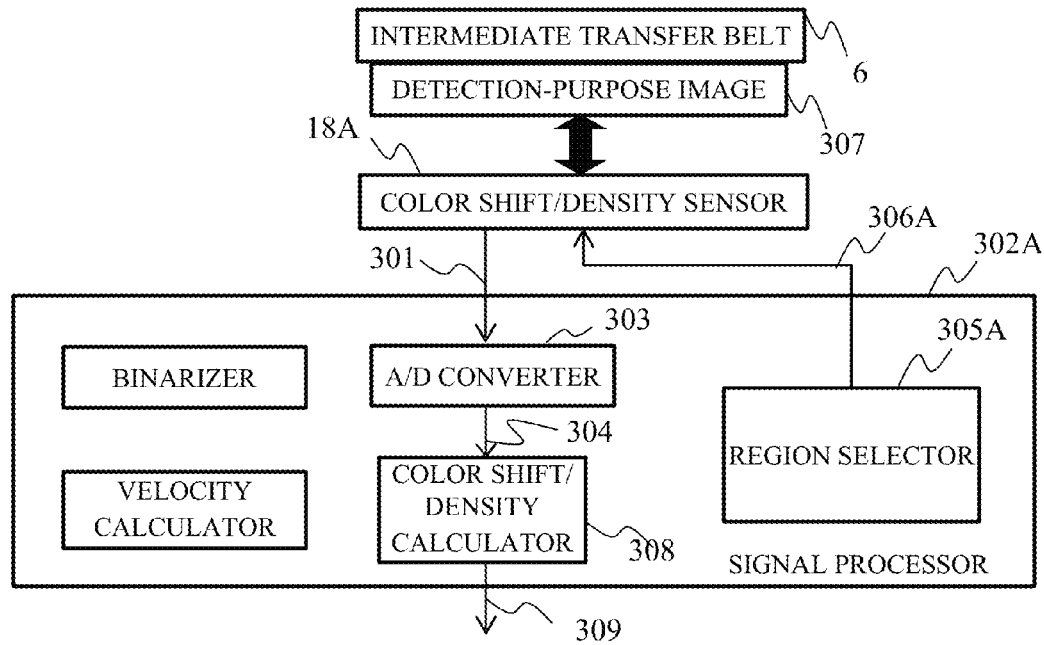
Figure 12C:
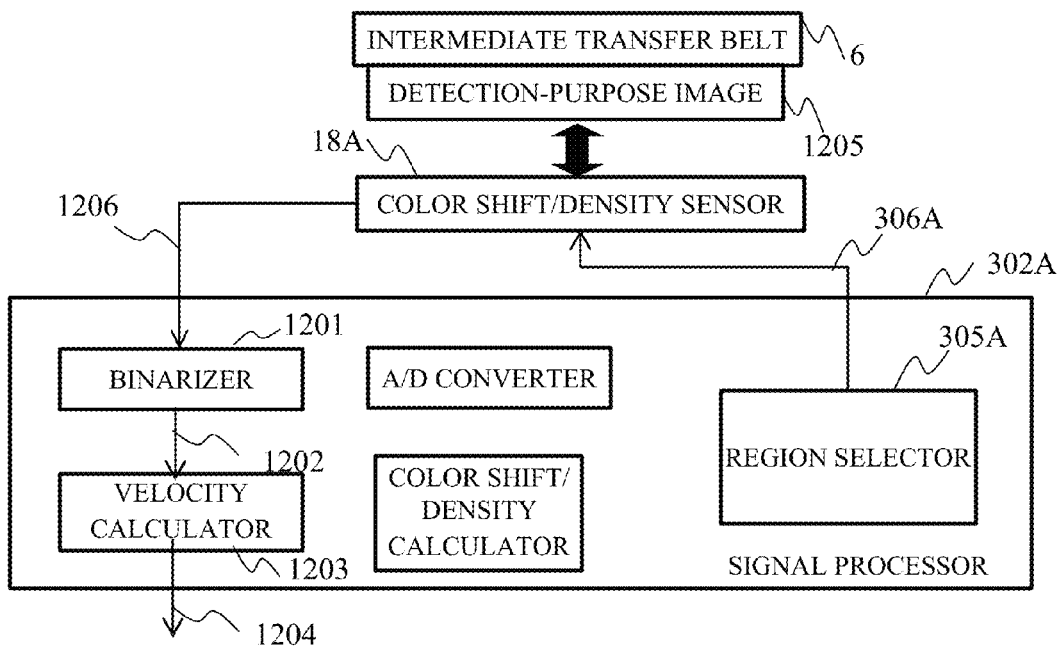

FIGS. 12A to 12C illustrate a configuration of the color shift/density detection apparatus of this embodiment, and FIG. 12A illustrates an operation of the color shift/density detection apparatus in selecting (setting) the specular reflection detection region. A signal processor 302A includes an A/D converter 303, a region selector 305A and a color shift/density calculator 308.

Figures 13A, 13B:
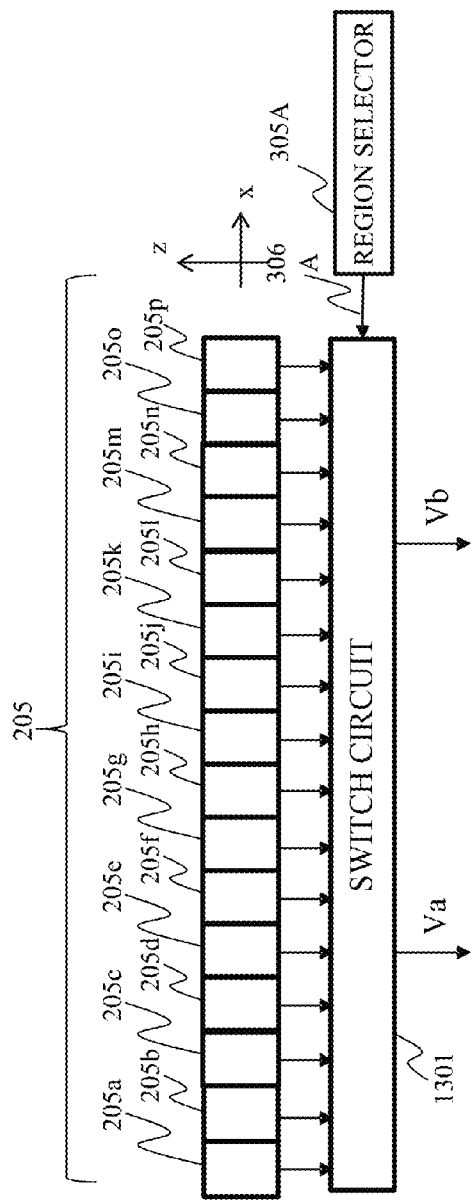
FIGS. 13A to 13F illustrate detection regions of a color shift/density sensor in Embodiment 2.

Although definitions of the specular reflection detection region and the diffuse reflection detection region in this embodiment are same as those in Embodiment 1, a switch circuit included in the sensor 18A is different from that in Embodiment 1. FIG. 13A illustrates the switch circuit. A basic configuration of the switch circuit in this embodiment is same as that of the switch circuit in Embodiment 1 and is different from that in Embodiment 1 in that output terminals to which outputs of 16 light-receiving elements (n=16) are connected are Va and Vb. On the other hand, FIG. 13B illustrates a relation between the output terminals connected with the output signals of the respective light-receiving elements and 2-bit switching signals each being region setting information 306A. For instance, a row indicated by a switching signal SW306(1,1) in FIG. 13B shows that, when the region setting information 306A is a 2-bit signal whose all bits are high level, the output signals of the light-receiving elements 205a to 205d and 205i to 205l are connected to the output terminal Va, and the output signals of the light-receiving elements 205e to 205h and 205m to 205p are connected to the output terminal Vb.

In this manner, the light-receiving element groups (referenced element groups) referenced by the sensor 18 are switched depending on the 2-bit switching signal as the region setting information 306A.

FIGS. 13C to 13F each illustrate the two sets of the referenced element groups 1301 and 1302 switched depending on the switching signal (region setting information 306A). Each set of the referenced element groups is constituted by two light-receiving element groups set so as to have an interval therebetween. A length of the referenced element group 1301 in an X direction is L1, and a length of the referenced element group 1302 in the X direction is L3.

Figure 13C:
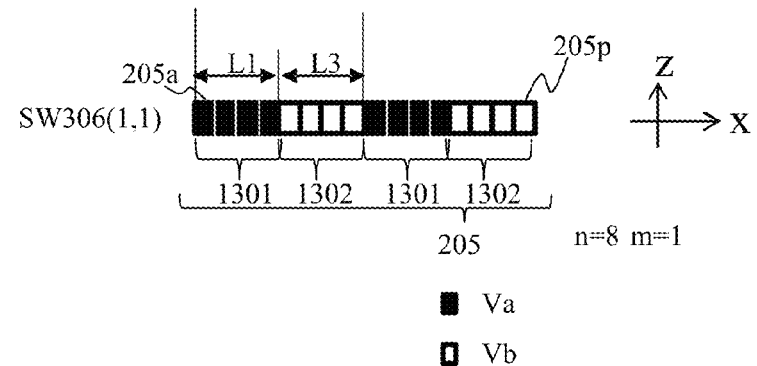
Figure 13D:
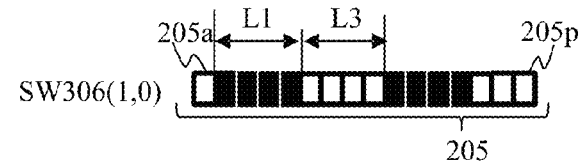

For instance, FIG. 13C shows a first set of (two) referenced element groups 1301 connected to the detected voltage value Va depending on the switching signal SW306(1,1) illustrated in FIG. 13B are filled in black, and a second set of (two) referenced element groups 1302 connected to the detected voltage value Vb depending thereon are filled in white. On the other hand, in FIG. 13D, a first set of (two) referenced element groups 1301 connected to the detected voltage value Va depending on a switching signal SW306(1,0) are filled in black, and a second set of (one) referenced element group 1302 connected to the detected voltage value Vb depending thereon is filled in white. In this case, one light-receiving element and three light-receiving elements, both of which are filled in white at left and right ends, are not used as ones constituting the referenced element group 1302.

As illustrated in FIGS. 13C to 13F, the region selector 305A in FIG. 12A sequentially shifts the light-receiving element groups each composed of a first number of (n/4=4 in this embodiment) light-receiving elements mutually adjacent in the X direction in units of light-receiving elements whose number is a second number (m=1 in this embodiment) equal to or less than the first number. Thereby, the region selector 305A sets four patterns of the two sets of the referenced element groups. Next, description will be made of a method of setting the specular reflection detection region in this embodiment. The region selector 305A compares, while shifting the two sets of (four or three) referenced element groups as described above, the detected voltage values Va and Vb output from the respective referenced element groups. Then, the region selector 305A selects (sets), as the specular reflection detection region that is a first light-receiving element group, one of the four or three referenced element groups from which a largest detected voltage value is output. The region selector 305A sets the other three or two referenced element groups as the diffuse reflection detection region as a second light-receiving element group. The sensor 18A outputs, as analog voltage values 301, the detected voltage value from the first light-receiving element group set to the specular reflection detection region as $V_{ref}$ and outputs the detected voltage value from the second light-receiving element group set to the diffuse reflection detection region as $V_{sca}$ to the signal processor 302A.

Since in this embodiment the two sets of the referenced element groups are arranged so as to have the 180-degree phase difference, shifting each referenced element group in units of light-receiving elements whose number is equal to or more than the number (4 in this embodiment) of the light-receiving elements constituting each referenced element group results in repetition of a state equivalent to a state in which the detected voltage values have been already compared to each other. This enables setting the specular reflection detection region with a smaller number of setting bits as compared to that in Embodiment 1.

Figure 13E:
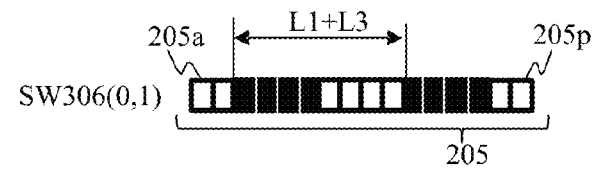
Figure 13F:
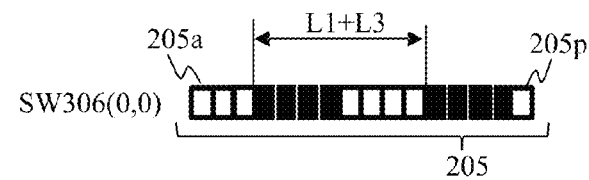

For instance, the state illustrated in FIG. 5A in Embodiment 1 corresponds to a state illustrated in FIG. 13E in this embodiment. That is, of the referenced element groups 1301 and 1302 set corresponding to the switching signal SW(0,1), the referenced element group 1302 filled in white is set to the specular reflection detection region, and the light-receiving element group filled in black is set to the diffuse reflection detection region. As just described, in this embodiment, it is possible to set at least the specular reflection detection region equivalently to that in Embodiment 1.

FIG. 12B illustrates an operation of the color shift/density detection apparatus performed in a state in which a color shift/density detection-purpose image (hereinafter simply referred to as "a detection-purpose image") 307, which is a toner image to be used for color shift/density detection, is formed on a surface of the intermediate transfer belt 6 facing the sensor 18A. In a same manner as that in Embodiment 1, the color shift/density calculator 308 detects a color shift and a density by using the detected voltage value $V_{ref}$ output from the specular reflection detection region in the sensor 18A and the detected voltage value $V_{sca}$ output from the diffuse reflection detection region in the sensor 18A.

Next, description will be made of a method of detecting a speed variation of the intermediate transfer belt 6 with reference to FIG. 12C, FIGS. 14A and 14B, FIGS. 15A to 15N and FIGS. 16A and 16B. FIG. 12C illustrates an operation of the color shift/density detection apparatus in the detection of the speed variation of the intermediate transfer belt 6. The signal processor 302A includes a binarizer 1201 and a speed calculator 1203.

The region selector 305A outputs, depending on the setting result of the specular reflection detection region, the region setting information (switching signal) 306A to the sensor 18 to set the specular reflection detection region in the multiple light-receiving elements on the sensor 18A. A detection-purpose image 1205 to be used to detect the speed variation of the intermediate transfer belt 6 is an image with a line-and-space patch pattern in which multiple lines are periodically formed in the X direction with spaces therebetween as illustrated in FIGS. 15A to 15N. The sensor 18A detects a variation in light amount of the reflected light caused by passage of the pattern, by light-receiving element groups switchably set as described later.

An analog single 1206 indicating the variation in reflected light amount detected by each light-receiving element group is input to the binarizer 1201 of the signal processor 302A and converted into a binary signal 1202. The binary signal 1202 is input to the speed calculator 1203.

The speed calculator 1203 detects times at which the binary signal 1202 changes between zero and one and calculates speed information 1204 of the intermediate transfer belt 6 from the detected times. The speed information 1204 is sent to the engine controller 17. The speed information 1204 is used as information for suppressing color shift in a formed image, such as information for controlling a timing at which the toner image is formed on the intermediate transfer belt 6 or information for controlling a rotational speed of the driving roller 7. Furthermore, in a product development stage, the image forming apparatus is designed to cancel various adverse effects of a rotational drive system on the color shift, such as eccentricities of rollers and an engagement period of gears. The speed information 1204 of the intermediate transfer belt 6 is used for evaluating the design.

Figure 14A:
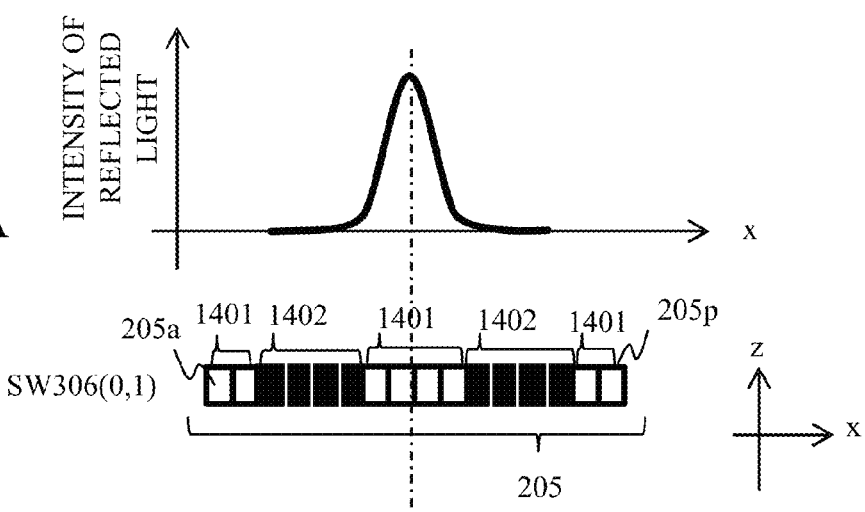
FIGS. 14A and 14B illustrate speed detection regions of the color shift/density sensor in Embodiment 2.

Next, with reference to FIGS. 14A and 14B, description will be made of switching setting of the multiple light-receiving element groups for detecting the speed variation of the intermediate transfer belt 6. FIG. 14A illustrates an example of an intensity distribution of the reflected light from the intermediate transfer belt 6 on the multiple light-receiving elements 205 in the sensor 18A. In this example, of the referenced element groups corresponding to the switching signal SW(0,1) which are illustrated in FIG. 13E, one referenced element group located at a center is selected as a first light-receiving element group (specular reflection detection region) 1401. Furthermore, the referenced element groups located across the first light-receiving element group are selected as the second light-receiving element group (diffuse reflection detection region) 1402.

Figure 14B:
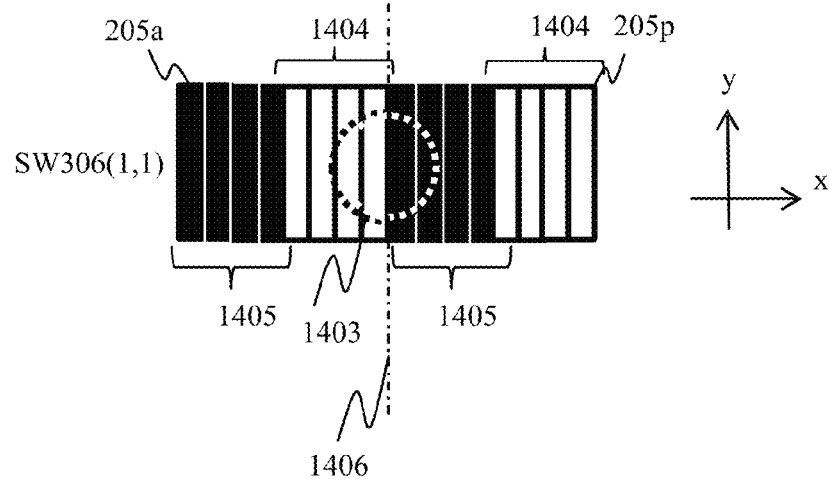

Thereafter, the region selector 305A shifts, from this state, a phase of the light-receiving element groups by 90 degrees as illustrated in FIG. 14B in order to detect the speed variation of the intermediate transfer belt 6. In FIG. 14B, a dotted circle indicates a reflected light spot 1403 formed by a reflected light from a light spot projected onto the intermediate transfer belt 6. The 90-degree phase shift sets a third light-receiving element group 1404 and a fourth light-receiving element group 1405 such that a boundary 1406 thereof is included in the reflected light spot 1403 on the first light-receiving element group 1401. The region selector 305A sets the third and fourth light-receiving element groups 1404 and 1405 as a detection region for detecting the speed (speed variation). In the example in FIG. 14B, the setting state of the referenced element groups corresponding to the switching signal SW(1, 1), which is illustrated in FIG. 13C, corresponds to a setting state for detecting the speed variation.

In the state illustrated in FIG. 14B, a detection-purpose image 1501 for detecting the speed variation is formed on the intermediate transfer belt 6. FIGS. 15A to 15G illustrate a variation with time of a relation between the detection-purpose image 1501 moved together with the intermediate transfer belt 6 by which the detection-purpose image 1501 is transported and the light spot 1502 projected onto the intermediate transfer belt 6. On the other hand, FIGS. 15H to 15N illustrate a variation with time of a relation between the third and fourth light-receiving element groups (detection regions) 1404 and 1405 and a projected image (black portion) 1503 of the detection-purpose image 1501 in the reflected light spot 1403 formed by the reflected light from the light spot 1502.

With the movement of the intermediate transfer belt 6, the line-and-space pattern that is the detection-purpose image 1501 transported thereby sequentially passes through a position of the light spot 1502. Since no light is detected at a projection portion in the detection region at which the projected image 1503 is present, the detected voltage value output from the detection region including the projection portion decreases. On the other hand, since the specularly reflected light from the intermediate transfer belt 6 is detected at a non-projection portion at which the projected image 1503 is not present, the detected voltage value output from the detection region not including the projection portion increases. The movement of the projected image 1503 on the detection regions (third and fourth light-receiving element groups 1404 and 1405) changes the detected voltage values output from these detection regions like periodic signals whose phases are mutually shifted.

Figure 16A:
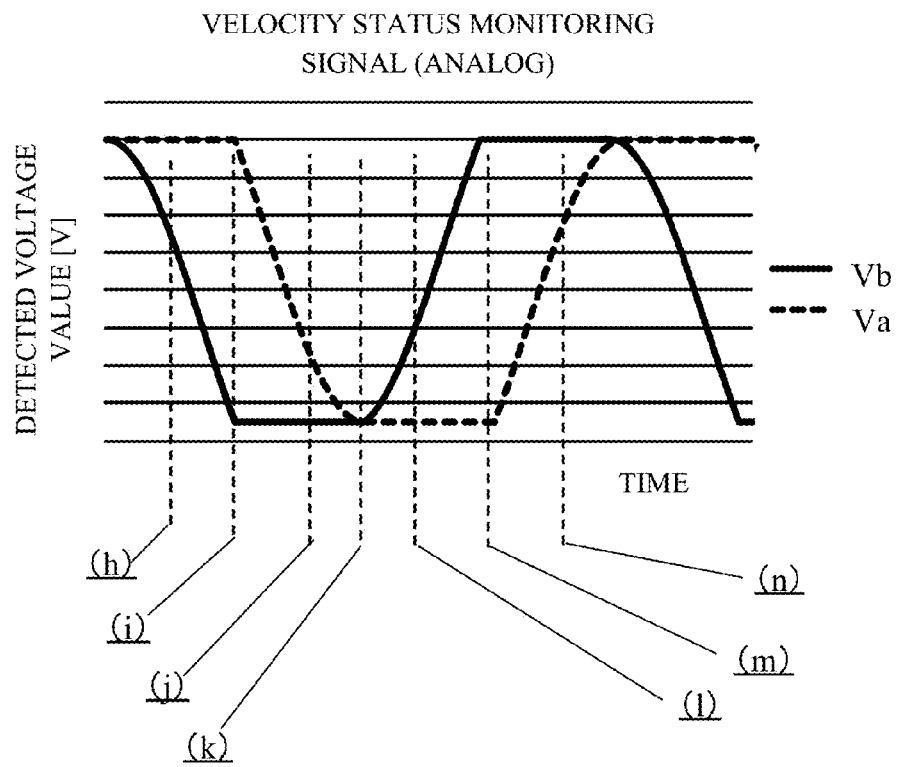
FIGS. 16A and 16B illustrate a signal output in each speed detection region in Embodiment 2.
Figure 16B:
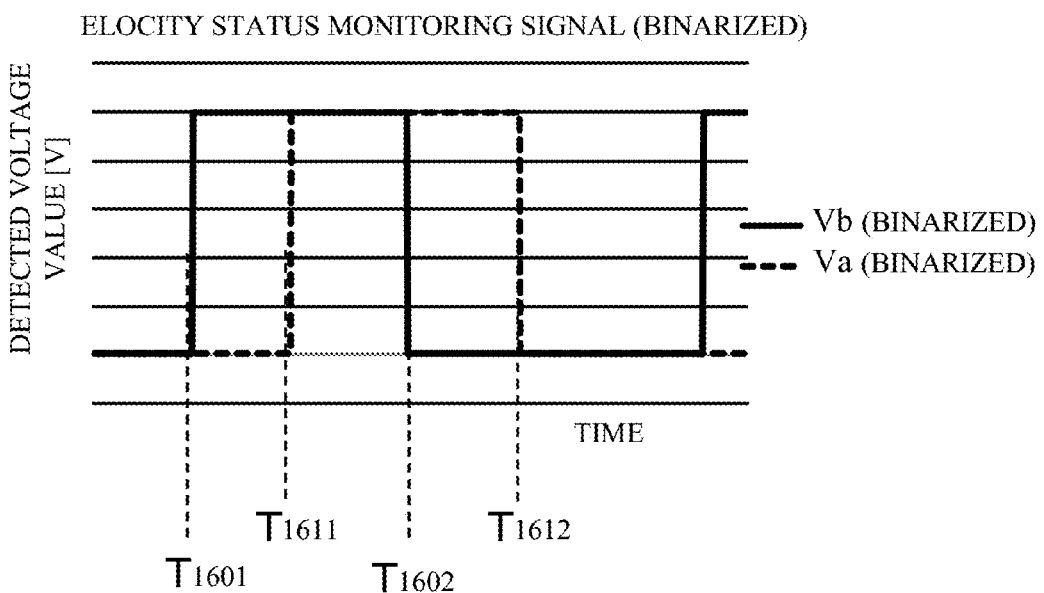

Next, with reference to FIGS. 16A and 16B, description will be made of a method of detecting the speed variation of the intermediate transfer belt 6. FIG. 16A illustrates variations with time of the voltage values (detected voltage values) Vb and Va of the analog signals 1206 output from the third and fourth light-receiving element groups 1404 and 1405 as the detection regions. Times denoted by symbols (h) to (n) respectively correspond to those in FIGS. 15H to 15N. FIG. 16B illustrates signal waveforms acquired by binarizing the detected voltage values Vb and Va with a threshold voltage value Vth (not illustrated). The speed calculator 1203 calculates a detection time at which the third light-receiving element group 1404 detects the projected image 1503 is calculated by averaging times $T_{1601}$ and $T_{1602}$ at which a polarity of the detected voltage value Vb changes. Similarly, the speed calculator 1203 calculates a detection time at which the fourth light-receiving element group 1405 detects the projected image 1503 by averaging times $T_{1611}$ and $T_{1612}$ at which a polarity of the detected voltage value Va changes. A projected image passage time ΔT expressed by following expression (16), which is a difference between the two projected image detection times Average $(T_{1612}, T_{1611})$ and Average$(T_{1602}, T_{1601})$ varies depending on a transported speed of the detection-purpose image 1501 for producing the projected image 1503, that is, a transporting speed V of the intermediate transfer belt 6.

$$V \propto \Delta T = \text{Average}(T_{1612}, T_{1611}) - \text{Average}(T_{1602}, T_{1601}) \quad (16)$$

For this reason, monitoring the projected image passage time ΔT and detecting its variation enables detecting a variation in the transporting speed V of the intermediate transfer belt 6 due to any abnormal transportation by the intermediate transfer belt 6.

Embodiment 3

Next, as Embodiment 3 of the present invention, description will be made of an alternative to the method of detecting the transporting speed of the intermediate transfer belt 6 using the sensor 18A that sets the two sets of the referenced element groups having the 180-degree phase difference, which was described in Embodiment 2. This embodiment enables detecting the transporting speed of the intermediate transfer belt 6 that is closer to an actual one as compared to that in Embodiment 2.

Figure 17A:
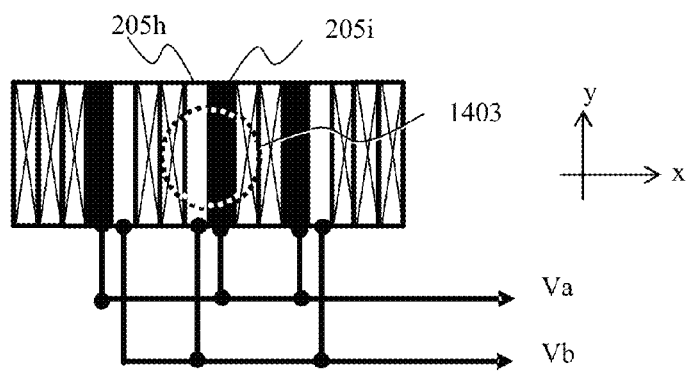
FIGS. 17A to 17K illustrate speed detection regions of a color shift/density sensor of a color shift/density detection apparatus that is Embodiment 3 of the present invention.
Figure 17B:
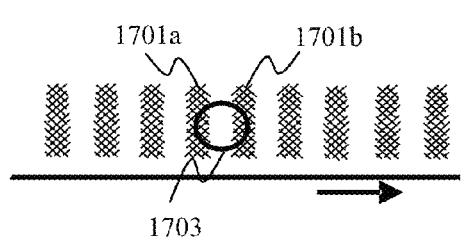
Figure 17F:
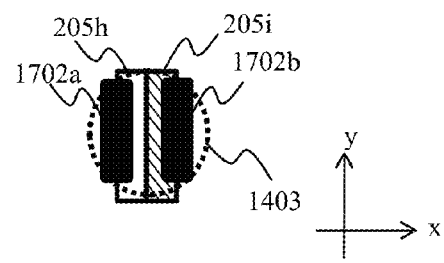
Figure 17C:
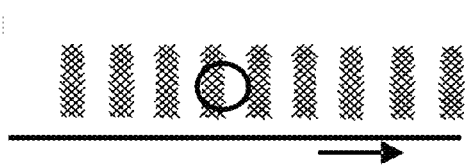

FIG. 17A illustrates setting of detection regions of the reflected light spot 1403 in the sensor 18A for detecting the transporting speed of the intermediate transfer belt 6. This embodiment is same as Embodiment 2 in that the reflected light spot 1403 is set so as to be formed across two detection regions. However, this embodiment is different from Embodiment 2 in number of light-receiving elements constituting each detection region. Specifically, this embodiment sets a width of each light-receiving element in a speed detection direction (x direction) to be smaller than a diameter of the reflected light spot 1403 on the sensor 18A to make detection times and detection positions of projected images 1702*a* and 1702*b* of detection-purpose images 1701*a* and 1701*b* illustrated in FIGS. 17B to 17E correspond to each other.

FIGS. 17B to 17E illustrate movement of the detection-purpose images 1701*a* and 1701*b* transported by the intermediate transfer belt 6 with respect to a light spot 1703 projected onto the intermediate transfer belt 6. FIGS. 17F to 17I illustrate the projected images 1702*a* and 1702*b* on light-receiving elements 205*h* and 205*i* as two detection regions across their boundary included in the reflected light spot 1403 on the sensor 18A in states respectively corresponding to FIGS. 17B to 17E. The light-receiving elements 205*h* and 205*i* correspond to third and fourth light-receiving element groups.

Figure 17G:
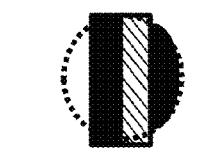
Figure 17D:
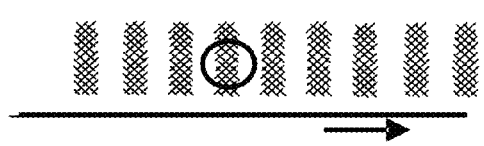
Figure 17H:
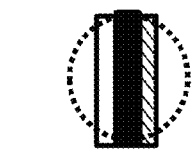
Figure 17E:
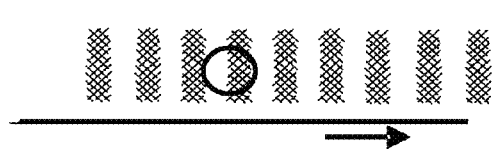
Figure 17I:
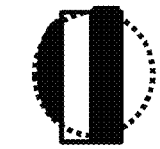
Figure 17J:
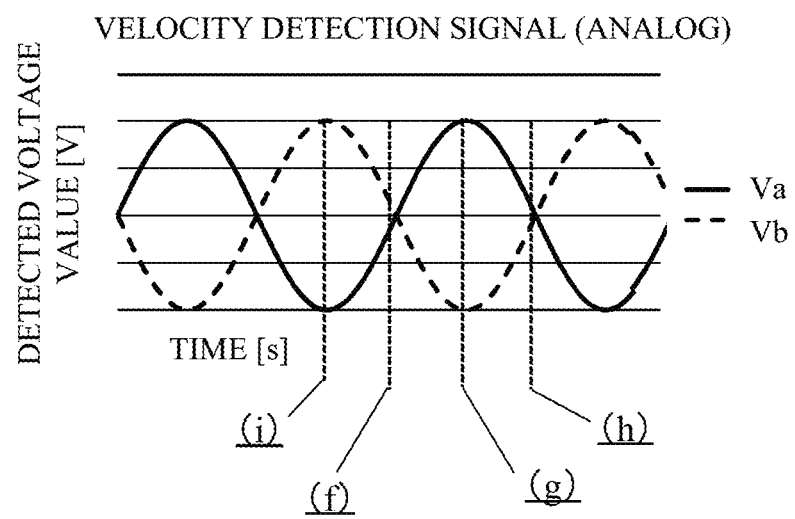
Figure 17K:
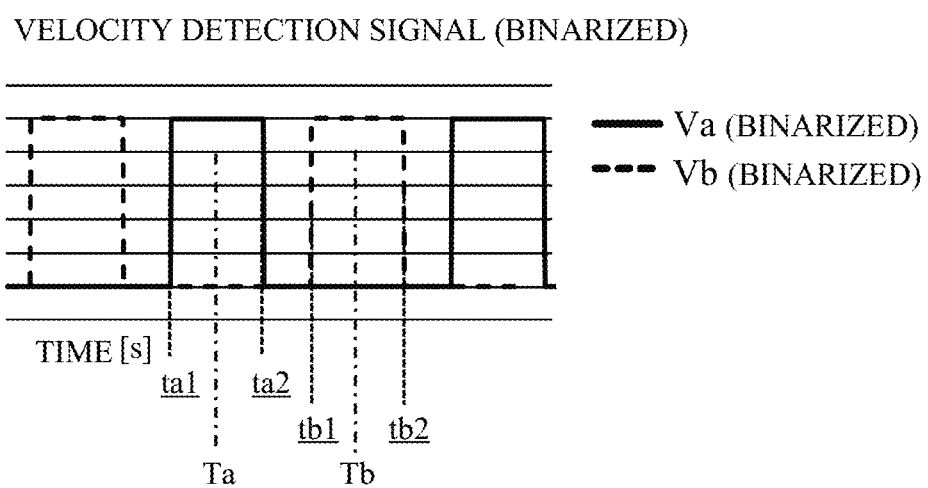

FIG. 17J illustrates detected voltage values Vb and Va output from the light-receiving elements 205*h* and 205*i* in the states illustrated in FIGS. 17F to 17I. Symbols (f) to (i) in the drawing represent times in the states illustrated in FIGS. 17F to 17I. FIG. 17J shows that amplitudes of the detected voltage values Vb and Va become smallest respectively in the state illustrated in FIG. 17G where the projected image 1702*a* is projected at a center of the light-receiving element 205*h* and in the state illustrated in FIG. 17I where the projected image 1702*b* is projected at a center of the light-receiving element 205*i* (in other words, one of the projected images overlaps one of the light-receiving elements). FIG. 17G illustrates a result of binarization of the detected voltage values Vb and Va. The speed calculator 1203 in this embodiment calculates average times Tb and Ta at which the projected images 1702*a* and 1702*b* pass through the centers of the light-receiving elements (detection regions) 205*h* and 205*i* by using times $t_{b1}$, $t_{b2}$, $t_{a1}$, and $t_{a2}$ at which polarities of the binary signals Vb and Va change. When a width of each light-receiving element in the x direction is D, the transporting speed of the intermediate transfer belt 6 is calculated by following expression (17):

$$V = \frac{1}{2} \times \frac{D}{Ta - Tb} \quad (17)$$

Figure 18B:
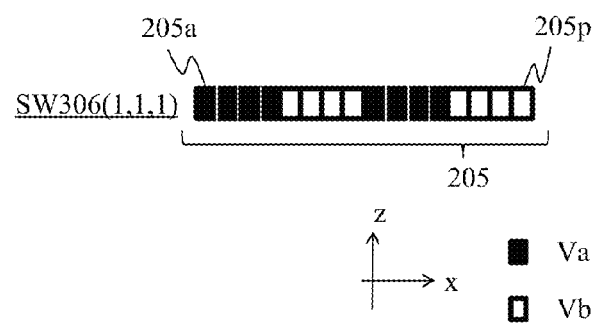
Figure 18C:
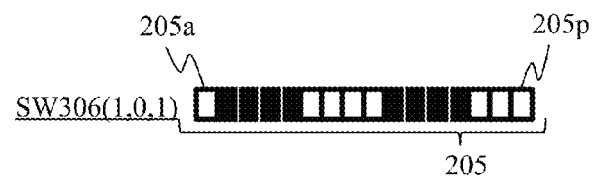
Figure 18D:
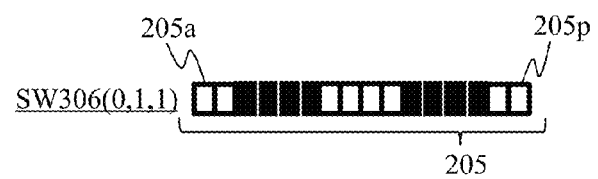
Figure 18E:
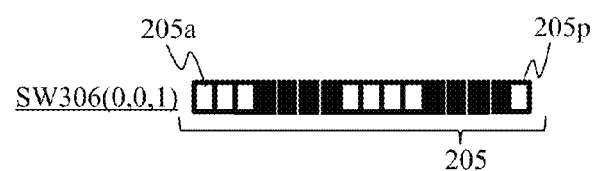
Figure 18F:
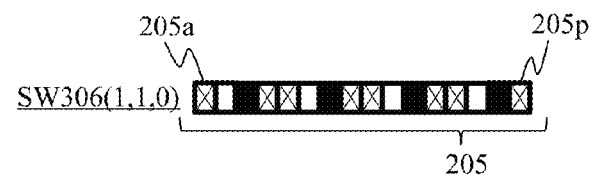
Figure 18G:
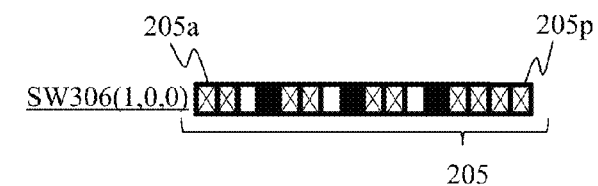

FIGS. 18A to 18I illustrate output terminals to which output signals of the light-receiving elements are connected and detection regions (hereinafter each referred to as "a speed detection region") for detecting the transporting speed of the intermediate transfer belt 6; the output terminals are switched depending on switching signals (region setting information). FIG. 18A illustrates a configuration for speed detection in this embodiment corresponding to the setting of the specular reflection detection region described in Embodiment 2. FIGS. 18B to 18I illustrate a speed detection region set corresponding to the output terminals for the output signals illustrated in FIG. 18A.

Depending on an entrance position of a specularly reflected light from the intermediate transfer belt 6 on the multiple light-receiving elements, a specular reflection detection region (black-filled region) illustrated in FIGS. 18B to 18E and a diffuse reflection detection region (white-filled region) are set. Then, the speed detection region is set for the respective region settings as illustrated in FIGS. 18F to 18I.

The speed detection region illustrated in FIGS. 18F to 18I is set, regardless of which light-receiving element group is selected as the specular reflection detection region, such that a calculation of a difference between the times to be used for calculating the transporting speed of the intermediate transfer belt 6 can be performed uniquely depending on a transporting direction of the intermediate transfer belt 6. For instance, the calculation of the time difference is expressed as (Ta−Tb) when the intermediate transfer belt 6 is transported in a +X direction and is expressed as (Tb−Ta) when the intermediate transfer belt 6 is transported in a −X direction.

This embodiment enables providing a color shift/density sensor 18A capable of detecting the transporting speed of the intermediate transfer belt 6.

When color shift detection and density detection are to be performed in this embodiment, same setting and process as those in Embodiment 2 may be performed.

Embodiment 4

Next, as Embodiment 4 of the present invention, description will be made of a method of detecting a variation in slope angle of a detection object surface (surface of the intermediate transfer belt 6) by utilizing the two sets of the light-receiving element groups arranged so as to have the 180-degree phase difference, which were described in Embodiment 2. This embodiment enables detecting, without using a patch, the variation in slope angle of the detection object surface and feeding a detection result back to an image forming process and a control process of a drive system in an image forming apparatus to improve an image quality.

A reflection sensor of this embodiment is capable of detecting the color shift and the density in the same manner as that in Embodiment 2 and of detecting the transporting speed of the intermediate transfer belt 6 in the same manner as that in Embodiment 3. This means that the single reflection sensor can achieve multiple types of detection functions.

Figure 19B:
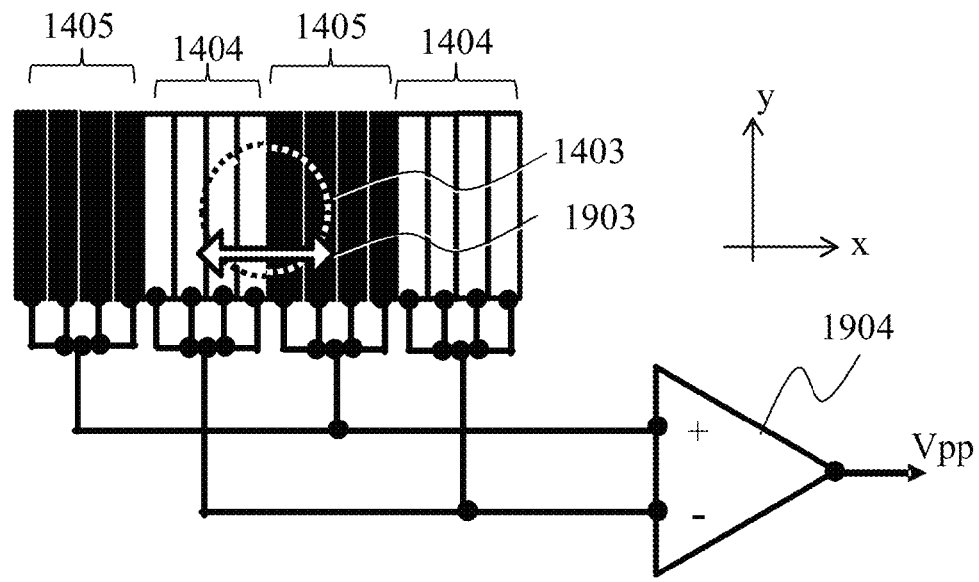
Figure 19C:
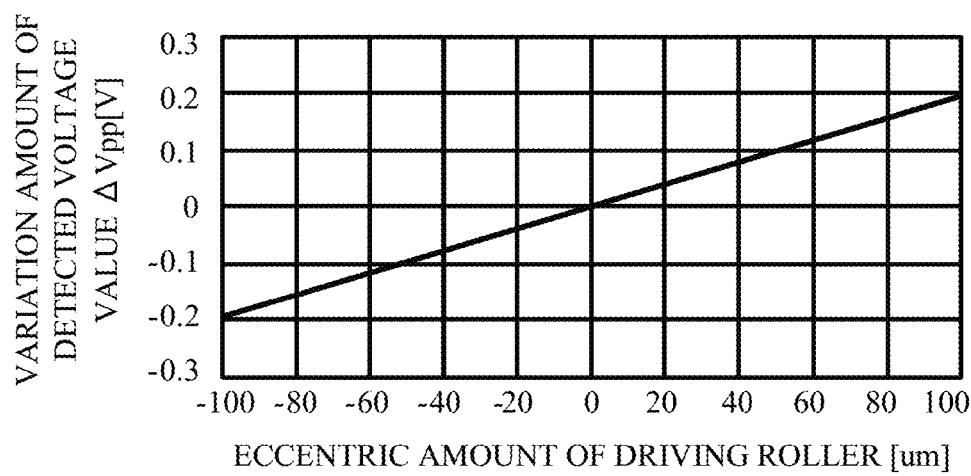

With reference to FIGS. 19A to 19C, description will be made of the method of detecting the variation in slope angle of the detection object surface. FIG. 19A illustrates a color shift/density sensor (hereinafter simply referred to as "a sensor") 18B disposed so as to face a surface (hereinafter referred to as "a belt curved surface") of a curved surface portion of the intermediate transfer belt 6 along a roller surface of a driving roller 7 around which the intermediate transfer belt 6 is wound.

A ray 401 emitted from a light source is reflected by the belt curved surface to enter a light-receiving element group 205 as a specularly reflected light 402. In this light entrance, an eccentric component 1901 of the driving roller 7 varies the slope angle of the belt curved surface as a tangent angle thereto, which causes a ray fluctuation 1902 in the reflected light.

FIG. 19B illustrates detection regions set in multiple light-receiving elements on the sensor 18B and a reflected light spot 1403 formed by the specularly reflected light 402 on the multiple light-receiving elements.

Since setting of the detection regions is identical to the setting of the detection regions to detect the speed variation described in Embodiment 2, a detailed description thereof is omitted. In the light-receiving elements on the sensor 18B, two third light-receiving element groups 1404 and two fourth light-receiving element groups 1405 are set. Outputs of the two third light-receiving element groups 1404 and outputs of the two fourth light-receiving element groups 1405 are respectively combined and input to a subtractor 1904. The subtractor 1904 subtracts the combined output of the third light-receiving element groups 1404 from the combined output of the fourth light-receiving element groups 1405 and outputs a subtraction result as a differential output voltage value Vpp.

The ray fluctuation 1902 caused by the eccentricity of the driving roller 7 results in a variation in position of the reflected light spot 1403. A positional shift of the reflected light spot 1403 from its normal position toward the third light-receiving element group 1401 increases the combined output of the third light-receiving element groups 1404 to be subtracted, which decreases the differential output voltage value Vpp. On the other hand, a positional shift of the light spot 1403 from the normal position toward the fourth-light-receiving element group 1405 decreases the combined output of the third light-receiving element groups 1404, which increases the differential output voltage value Vpp.

FIG. 19C illustrates a relation between the eccentricity 1901 of the driving roller 7 and the differential output voltage value Vpp. Depending on the variation in position of the reflected light spot 1403 caused by the variation in slope angle of the belt curved surface due to the eccentricity 1901 of the driving roller 7, the differential output voltage value Vpp varies. For this reason, a variation in eccentric state of the driving roller 7 can be detected from the variation of the differential output voltage value Vpp during the transportation of the intermediate transfer belt 6. The detection of the variation in eccentric state of the driving roller 7 enables detecting the variation in transporting speed of the intermediate transfer belt 6 caused by the eccentricity of the driving roller 7. Utilizing detected information on the speed variation to control a forming timing of a toner image and a rotational speed of the driving roller 7 enables suppressing generation of the color shift.

Differently from Embodiments 2 and 3, this embodiment enables detecting the variation in transporting speed of the intermediate transfer belt 6 due to the eccentricity of the driving roller 7 without using a detection-purpose image, namely, a toner image. This enables speed variation detection with fewer toner consumption and fewer system-related limitations on detection sequence.

Embodiment 5

Next, as Embodiment 5 of the present invention, description will be made of a detection structure which suppresses an amount of a ray fluctuation generated by a variation in slope angle of a surface of a detection object (a surface of an intermediate transfer belt 6) that is an object and which suppresses undesirable entrance of a diffusely reflected light into a specular refection detection region. This embodiment enables shortening a required length of a light-receiving region, miniaturizing a reflection detection apparatus and improving an S/N ratio.

This embodiment enables detecting color shift and density in the same manner as that in Embodiment 2 and detecting a transporting speed of the intermediate transfer belt 6 in the same manner as that in Embodiment 3. In addition, this embodiment enables detecting the variation in slope angle of the surface of the detection object at a sensitivity lower than that in Embodiment 4 in the same manner as that in Embodiment 4. Moreover, this embodiment enables achieving multiple detection functions by a single reflection sensor and miniaturizing the refection sensor.

Figure 20A:
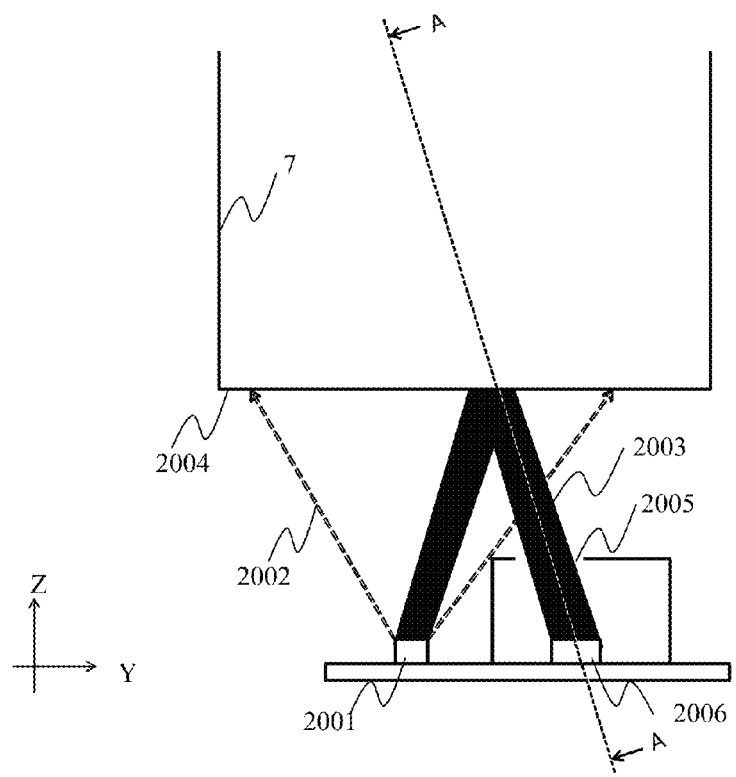
FIGS. 20A to 20C illustrate a configuration of a color shift/density detection apparatus that is Embodiment 5 of the present invention and a ray fluctuation.
Figure 20B:
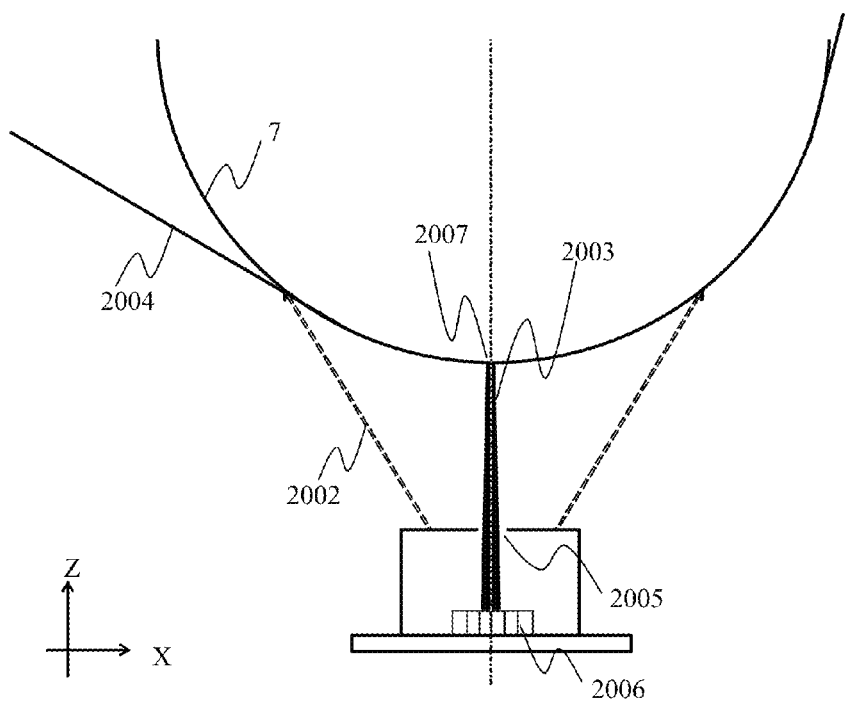
Figure 20C:
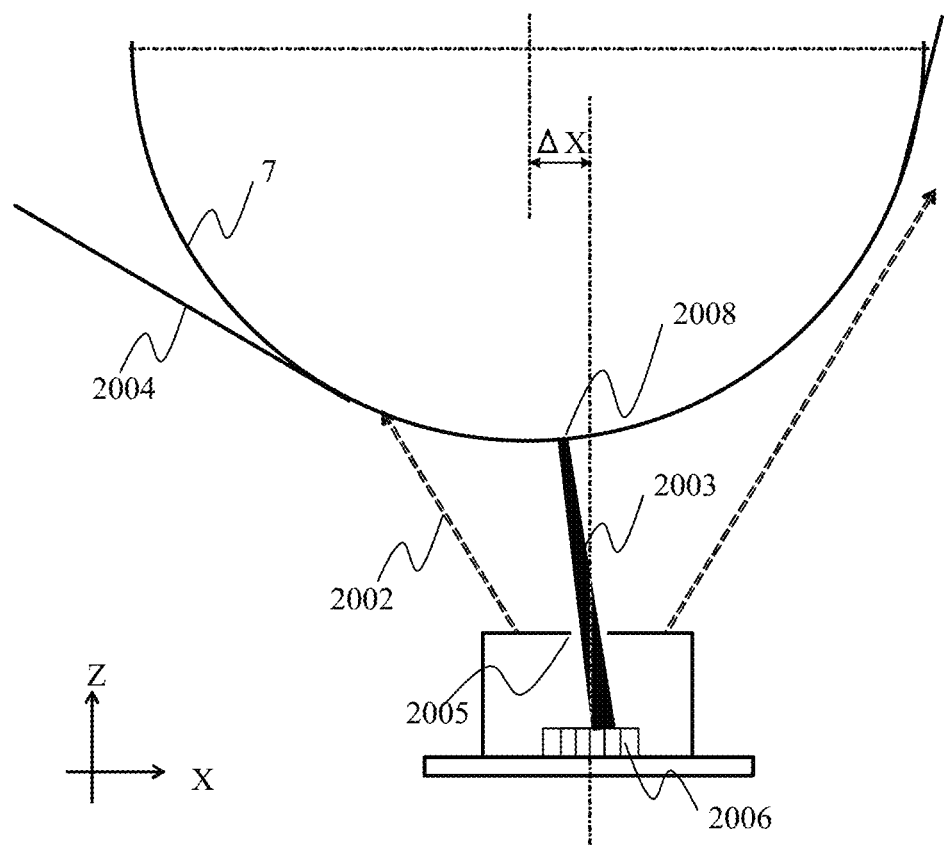

With reference to FIGS. 20A to 20C, description will be made of a mechanism of the generation of the ray fluctuation of a reflected light in a configuration of the refection sensor of this embodiment. FIG. 20A is a drawing illustrating the configuration of the reflection sensor of this embodiment. FIG. 20A illustrates a color shift/density sensor (hereinafter simply referred to as "a sensor") disposed so as to face a surface (hereinafter referred to as "a belt curved surface") of a driving roller 7 around which the intermediate transfer belt is wound. Of a diverging light flux 2002 emitted from a light source 2001, a specularly reflected light 2003 is reflected by a belt curved surface 2004 to pass through an aperture portion 2005 and then enter multiple light-receiving elements.

FIGS. 20B and 20C illustrate a difference between ray fluctuations generated on an A-A cross section shown in FIG. 20A caused by a relative positional difference between the sensor and the roller.

In FIG. 20B, a rotation axis of the driving roller 7 and a center of the sensor are on an identical axis in a Z axis direction. The specularly reflected light 2003 on the belt curved surface 2004 is reflected at a light-reflecting point 2007 on the axis to enter a center of the multiple light-receiving elements.

FIG. 20C illustrates a state in which the center of the sensor is shifted in parallel to the rotation axis of the driving roller 7 by a distance ΔX in an X axis direction. In this state, a position of a light-reflecting point 2008 of the specularly reflected light 2003 to reach the multiple light-receiving elements that is located on the belt curved surface 2004 depends on a state of the slope of the belt curved surface 2004. This embodiment provides no aperture limitation on a light-source-side light flux or allows the light flux to be sufficiently introduced to a region including the light-reflecting point 2008 even if the aperture limitation is provided. This structure enables the detection with the multiple light-receiving elements from the specularly reflected light passing through the aperture portion 2005.

Although a point at which the specularly reflected light enters the multiple light-receiving elements varies depending on a positional relation among constituent elements that may affect the above-described light-reflecting point 2008, it is only necessary to select, by the method described in Embodiment 1, a first light-receiving element group that the specularly reflected light 2006 enters. The diffusely reflected light reaching the first light-receiving element group is suppressed by the aperture portion 2005, which suppresses a decrease in a detection spatial frequency and improves an S/N ratio of a signal. Since a diffusely reflected light 2009 indicated as an example by a solid line reaches other light-receiving element groups different from the first light-receiving element group, a second light-receiving element group may be freely selected from the light-receiving element groups other than the first light-receiving element group. When a light amount of the specularly reflected light is to be detected, multiplying the light amount detected by the second light-receiving element group by a coefficient corresponding to a diffusely reflected light component detected by the first light-receiving element group and subtracting a value of the coefficient from the light amount detected by the first light-receiving element group enables calculating, with a higher accuracy, the light amount of the specularly reflected light detected by the first light-receiving element group.

As described above, the configuration in this embodiment enables, because of an effect provided by the aperture portion 2005 and the light source 2001 widely illuminating the object, suppressing the amount of the ray fluctuation generated on the multiple light-receiving elements, suppressing the diffusely reflected light reaching the selected first light-receiving element group, miniaturizing the sensor and improving the S/N ratio.

Instead of the diverging light flux described in this embodiment, a collimated light flux may be emitted from the light source.

An additional description will now be made of an effect provided, in a relation among the light source, the belt curved surface onto which the light is to be projected and the light-receiving elements, by miniaturization of the light-receiving elements in a configuration having a so-called light-receiving aperture in which the aperture is provided between the belt curved surface and the light-receiving elements. In the configuration of this embodiment having the light-receiving aperture, a geometrical ray path of the specularly reflected light depends on a size and a position of the light source, the slope of the belt curved surface as the object, and a position and a size of the aperture as described above. In this configuration, although the ray path varies depending on a positional relation among the light source, the belt curved surface as the object and the light-receiving aperture with a tolerance, a position at which the ray reaches the light-receiving elements on a ray return path varies in principle with the light-receiving aperture being a reference point.

On the other hand, in a configuration having a light source aperture in which the aperture is provided between the light source and the belt curved surface, a geometrical ray forward path depends on a positional relation between the light source and the light source aperture. Consequently, a return geometrical ray path depends on the slope of the belt curved surface onto which the ray is projected, which defines a position at which the ray reaches the light-receiving elements.

A comparison of the configuration having the light receiving aperture and the configuration having the light source aperture shows that the former has an optical path from the aperture portion to the light-receiving elements which is obviously shorter than that of the latter and that the former in which the aperture is provided on a return-path side with respect to the belt curved surface reflecting the ray that largely affects the ray path, suppresses a ray path fluctuation on the light-receiving elements more compared to the latter and thus suppresses a variation in the position at which the ray enters the light-receiving elements. For this reason, employing the configuration having the light-receiving aperture enables miniaturizing the light-receiving elements.

Although each of the above embodiments described the case where the line sensor constituted by the multiple light-receiving elements arranged in line in a one-dimensional direction is used as the color shift/density sensor (reflection sensor), an area image sensor constituted by two-dimensionally arranged multiple light-receiving elements may alternatively be used as the color shift/density sensor. Furthermore, although each of the above embodiments described the case where the diffuse reflection detection region is set on the multiple light-receiving elements of the color shift/density sensor, a light-receiving unit may be provided outside a path of the specularly reflected light different from that for the multiple light-receiving elements and used as the diffuse reflection detection region.

Moreover, although each of the above embodiments described the case where the reflection detection apparatus is used to detect the density and color shift of the toner and others in the image forming apparatus, the reflection detection apparatus may be used for various apparatuses each including an operation portion performing its operation by using output of the reflection detection apparatus.

Each of the above embodiments enables accurately detecting the light amount of the specularly reflected light without an increase of the area of the light-receiving region even if the ray fluctuation of the specularly reflected light is generated. Using the detection result enables detecting, with high accuracy, the density of the toner, the color shift of the toner, the movement speed of the transferred body, a variation of the slope of the transfer body and others in an image forming apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-096319, filed on May 7, 2014, which is hereby incorporated by reference herein in its entirety.

What is claimed is:

1. A reflection detection apparatus comprising:
multiple light-receiving elements configured to detect a pattern formed on an object by receiving a reflected light from the object; and
a selector configured to select a first light-receiving element group from the multiple light-receiving elements,
wherein the selector is configured to select the first light-receiving element group that includes plural light-receiving elements each mainly receiving a specularly reflected light from an area of the object where no pattern is formed among the multiple light-receiving elements, on a basis of outputs from the multiple light-receiving elements,
the detection of the pattern is made on a basis of an output from the first light-receiving element group, and
the selector is configured to be capable of shifting the first light-receiving element group in units of light-receiving elements whose number is less than that of the light-receiving elements included in the first light-receiving element group.

2. A reflection detection apparatus according to claim 1, wherein an aperture portion limiting a light flux is disposed between the multiple light-receiving elements and the object.

3. A reflection detection apparatus according to claim 1, wherein the selector is configured to:
select multiple light-receiving element groups in a direction in which the multiple light-receiving elements are arranged, the multiple light-receiving element groups (a) each including mutually adjacent light-receiving elements whose number is a first number and (b) being mutually shifted by plural light-receiving elements whose number is a second number equal to or smaller than the first number; and
set the multiple light-receiving element groups as the first light-receiving element group.

4. A reflection detection apparatus according to claim 1, further comprising a pattern interval calculator configured to:
sequentially detect, by using the outputs from the first light-receiving element group, multiple patterns formed on the object as a moving object; and
calculate a position of each of the multiple patterns on the moving object by using times at which the respective patterns are detected.

5. A reflection detection apparatus according to claim 1, wherein the selector is configured to select, from the multiple light-receiving elements on the basis of the outputs thereof, a second light-receiving element group including plural light-receiving elements each mainly receiving a diffusely reflected light more than the specularly reflected light.

6. A reflection light detection apparatus according to claim 5, wherein the selector is configured to:
select multiple light-receiving element groups in a direction in which the multiple light-receiving elements are arranged, the multiple light-receiving element groups (a) each including mutually adjacent light-receiving elements whose number is a first number and (b) being mutually shifted by plural light-receiving elements whose number is a second number equal to or smaller than the first number;
set the multiple light-receiving element groups as the first light-receiving element group; and
set the second light-receiving element group from non-selected light-receiving element groups.

7. A reflection detection apparatus according to claim 5, wherein the selector is configured to select the second light-receiving element group such that the second light-receiving element group has a wider light-receiving area than that of the first light-receiving element group.

8. A reflection detection apparatus according to claim 5, further comprising a pattern interval calculator configured to:
sequentially detect, by using the outputs from the first and second light-receiving element groups, multiple patterns formed on the object as a moving object; and
calculate intervals of the multiple patterns on the moving object by using times at which the respective patterns are detected.

9. A reflection detection apparatus according to claim 5, further comprising a specular reflection calculator configured to calculate, by using the outputs from the first and second light-receiving element groups, an output component corresponding to the specularly reflected light in the outputs from the first and second light-receiving element groups.

10. A reflection detection apparatus according to claim 5, wherein:
the selector is configured to set a third light-receiving element group and a fourth light-receiving element group in the first light-receiving element group; and
the apparatus further comprises:
a speed calculator configured to:
sequentially detect, by using the outputs from the third and fourth light-receiving element groups, multiple patterns formed on the object as a moving object; and
calculate a moving speed of the moving object by using a difference between times at which the respective patterns are detected.

11. A reflection detection apparatus according to claim 5, wherein the selector is configured to:
set a third light-receiving element group and a fourth light-receiving element group in the first light-receiving element group, and
detect a variation in slope of the object by using a difference between the outputs from the third and fourth light-receiving element groups.

12. An apparatus comprising:
a reflection detection apparatus; and
an operation unit configured to operate by using an output from the reflection detection apparatus,
wherein the reflection detection apparatus comprises:
multiple light-receiving elements configured to detect a pattern formed on an object by receiving a reflected light from the object; and
a selector configured to select a first light-receiving element group from the multiple light-receiving elements,
wherein the selector is configured to select the first light-receiving element group that includes plural light-receiving elements each mainly receiving a specularly reflected light from an area of the object where no pattern is formed among the multiple light-receiving elements, on a basis of outputs from the multiple light-receiving elements,
the detection of the pattern is made on a basis of an output from the first light-receiving element group, and
the selector is configured to be capable of shifting the first light-receiving element group in units of light-receiving elements whose number is less than that of the light-receiving elements included in the first light-receiving element group.

13. An image forming apparatus comprising:
a reflection detection apparatus;
a transfer body on which a latent image to which toner is adhered is formed; and
a detector configured to detect, by using an output from the reflection detection apparatus, at least one of a density of the toner, a color shift of a toner image, a moving speed of the transfer body and a variation in slope of the transfer body, wherein the reflection detection apparatus comprises:

multiple light-receiving elements configured to detect a pattern formed on the transfer body by receiving a reflected light from the transfer body; and a selector configured to select a first light-receiving element group from the multiple light-receiving elements, wherein the selector is configured to select the first light-receiving element group that includes plural light-receiving elements each mainly receiving a specularly reflected light from an area of the transfer body where no pattern is formed among the multiple light-receiving elements, on a basis of outputs from the multiple light-receiving elements, the detection of the pattern is made on a basis of an output from the first light-receiving element group, and the selector is configured to be capable of shifting the first light-receiving element group in units of light-receiving elements whose number is less than that of the light-receiving elements included in the first light-receiving element group.

14. A reflection detection apparatus comprising:

multiple light-receiving elements configured to detect a pattern formed on an object by receiving a reflected light from the object; and a selector configured to select a second light-receiving element group from the multiple light-receiving elements, wherein the selector is configured to select the second light-receiving element group that includes plural light-receiving elements each mainly receiving a diffusely reflected light from an area of the object where patterns are formed among the multiple light-receiving elements, on a basis of outputs from the multiple light-receiving elements, the detection of the pattern is made on a basis of an output from the second light-receiving element group, and the selector is configured to be capable of shifting the second light-receiving element group in units of light-receiving elements whose number is less than that of the light-receiving elements included in the second light-receiving element group.

15. An apparatus comprising:

a reflection detection apparatus; and an operation unit configured to operate by using an output from the reflection detection apparatus, wherein the reflection detection apparatus comprises:

multiple light-receiving elements configured to detect a pattern formed on an object by receiving a reflected light from the object; and a selector configured to select a second light-receiving element group from the multiple light-receiving elements, wherein the selector is configured to select the second light-receiving element group that includes plural light-receiving elements each mainly receiving a diffusely reflected light from an area of the object where patterns are formed among the multiple light-receiving elements, on a basis of outputs from the multiple light-receiving elements, the detection of the pattern is made on a basis of an output from the second light-receiving element group, and the selector is configured to be capable of shifting the second light-receiving element group in units of light-receiving elements whose number is less than that of the light-receiving elements included in the second light-receiving element group.

16. An image forming apparatus comprising:

a reflection detection apparatus;

a transfer body on which a latent image to which toner is adhered is formed; and a detector configured to detect, by using an output from the reflection detection apparatus, at least one of a density of the toner, a color shift of a toner image, a moving speed of the transfer body and a variation in slope of the transfer body, wherein the reflection detection apparatus comprises:

multiple light-receiving elements configured to detect a pattern formed on the transfer body by receiving a reflected light from the transfer body; and a selector configured to select a second light-receiving element group from the multiple light-receiving elements, wherein the selector is configured to select the second light-receiving element group that includes plural light-receiving elements each mainly receiving a diffusely reflected light from an area of the transfer body where patterns are formed among the multiple light-receiving elements, on a basis of outputs from the multiple light-receiving elements, the detection of the pattern is made on a basis of an output from the second light-receiving element group, and the selector is configured to be capable of shifting the second light-receiving element group in units of light-receiving elements whose number is less than that of the light-receiving elements included in the second light-receiving element group.

* * * * *